US007241617B2

(12) United States Patent
Fukumura et al.

(10) Patent No.: US 7,241,617 B2
(45) Date of Patent: *Jul. 10, 2007

(54) SENDAI VIRAL VECTORS COMPRISING FOREIGN GENES INSERTED BETWEEN THE R1 AND R2 LOCI

(75) Inventors: Masayuki Fukumura, Tsukuba (JP); Makoto Asakawa, Toyonaka (JP); Mamoru Hasegawa, Tsukuba (JP); Masayuki Shirakura, Tsukuba (JP)

(73) Assignee: DNAVEC Research, Inc., Ibaraki (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/843,922

(22) Filed: Apr. 30, 2001

(65) Prior Publication Data

US 2002/0012995 A1    Jan. 31, 2002

Related U.S. Application Data

(63) Continuation-in-part of application No. 09/720,979, filed as application No. PCT/JP99/03552 on Jul. 1, 1999, now abandoned.

(30) Foreign Application Priority Data

Jul. 3, 1998    (JP)    ............................... 10/204333

(51) Int. Cl.
*C12N 15/00* (2006.01)
*C07H 21/02* (2006.01)
*C07H 21/04* (2006.01)
*A01N 63/00* (2006.01)
*A01N 65/00* (2006.01)
*A01N 43/04* (2006.01)
*A61K 31/70* (2006.01)

(52) U.S. Cl. ................. 435/320.1; 536/23.1; 536/23.5; 536/23.51; 424/93.1; 514/44

(58) Field of Classification Search ............... 536/23.1; 514/44; 424/93.1; 800/21; 822/21
See application file for complete search history.

(56) References Cited

U.S. PATENT DOCUMENTS

| 5,631,237 | A  | * | 5/1997 | Dzau et al. ..................... 514/44 |
| 5,789,245 | A  | * | 8/1998 | Dubensky et al. ........ 435/320.1 |
| 6,451,579 | B1 |   | 9/2002 | Jessee et al. |
| 6,514,728 | B1 | * | 2/2003 | Kai et al. .................. 435/69.5 |
| 2002/0100066 | A1 | * | 7/2002 | Nagai et al. .................... 800/8 |
| 2003/0008399 | A1 |   | 1/2003 | Jessee et al. |
| 2003/0053988 | A1 |   | 3/2003 | Renner et al. |

FOREIGN PATENT DOCUMENTS

| EP | 0753202 | 9/1998 |
| EP | 0864645 | 9/1998 |
| EP | 0936531 | 8/1999 |
| EP | 1 186 667 A1 | 3/2002 |
| JP | 2000057327 | 2/2000 |
| WO | WO 97/16539 A1 | 5/1997 |
| WO | 0011834 | 3/2000 |
| WO | WO 00/70070 A1 | 11/2000 |
| WO | WO 01/20989 A1 | 3/2001 |

OTHER PUBLICATIONS

Deonarain (1998) Exp. Opin. Ther. Pat., 8(1): 53-69.*
Gorecki (2001) Exp. Opin. Emerging Drugs, 6(2): 187-98.*
Eck, et al. (1996) Goodman & Gilman's The Pharmacological Basis of Therapeutics, 9th Ed., McGraw-Hill, New York, NY., pp. 77-101.*
Lamb, et al (2001) Fundamental Virology, 4th Ed., Lippinocott and Wilkins, New York, NY, p. 691.*
Yonemitsu,et al (2002) Surgery, 131(Supp. 1): S261-S268.*
Nakanishi, et al. (1999) Mol. Membr. Biol., 16: 123-27.*
Hasan, et al. (1997) 78: 2813-20.*
Crystal (1995) Science, 270: 404-410.*
Gura (1997) Science, 278: 1041-42.*
Mandel, et al. (2003) CNS Drugs, 17(10): 729-62.*
Nobuyuki, et al. (2004) Trends in Genetics, 20(11): 563-69, pp. 563-64, paragraph bridging.*
Clements, et al. (1993) Oncogene, 8(5): 1311-16.*
Srinivasula, et al. (1996) Proc. Natl. Acad. Sci., USA., 93: 14486-91.*
Duckett, et al. (1996) EMBO. J., 15(11): 2685-94.*
Hudgins, et al. (1998) Exp. Neurol., 150: 171-82.*
Hearn, et al. (1998) Dev. Biol., 197: 93-105.*
Schendel, et al. (1997) Proc. Natl. Acad. Sci., USA., 94: 5113-18.*
Datta, et al. (1997) J. Biol. Chem., 272(3): 1965-69.*
Kobayashi, et al. (1997) Exp. Brain Res., 116: 315-25.*
Teng, et al. (1998) Euro. J. Neurosci., 10: 798-802.*
Winkler, et al. (1998) Brain Res., 788: 1-12.*
Calain, et al. (1993) J. Virol., 67(8): 4822-30.*
Sakai, et al. (1999) FEBS Lett., (1999) 456: 221-26.*
Anderson, W. F., *Nature*, 292(6679 Suppl): 25-30 (1998).
Verma, I.M. et al., *Nature*, 389(6648): 239-242 (1997).
Palu, G. et al., *Journal of Biotechnology*, 68(1): 1-13 (1999).
Crystal, R.G., *Science*, 270(5235): 404-410 (1995).
Gura, T., *Science*, 278(5340): 1041-1042 (1997).
Grifman M., et al., "Functional redundancy of acetylcholinesterase and neuroligin in mammalian neuritogenesis", *Proc. Natl. Acad. Sci. USA*, 95(23), pp. 13935-13940 (1998).
De Fiebre CM, et al., *Neurochem.* 18(10): 1089-94 (1993).
Nakanishi M, et al. *J. Control Release* 54(1): 61-8 (1998).
Miyazaki, H., et al., "Glial Cell Lin-Derived Neurotrophic Factor Protects Against Delayed Neuronal Death After Transient Forebrain Ischemia In Rats", *Neuroscience*, 89 (3), 643-647 (1999).

(Continued)

*Primary Examiner*—Joseph Woitach
*Assistant Examiner*—Robert M. Kelly
(74) *Attorney, Agent, or Firm*—Sterne, Kessler, Goldstein & Fox P.L.L.C.

(57) ABSTRACT

Use of a negative-sense RNA virus vector has enabled transfer of nucleic acid into nerve cells. The method of this invention can be used for introducing a gene efficiently into nerve cells including the central nerve tissue in gene therapy, etc.

4 Claims, 12 Drawing Sheets

OTHER PUBLICATIONS

Oomura, Y., "Physiological Effects of Endogenous Satiety Substances on Brain," Inst. Of Bio-Active Science, Nippon Zoki Pharmaceutical (1998); 20: 567-575 (with English explanation).

Wu P., et al., "Sendai virosomal infusion of an adeno-associated virus derived construct containing neuropeptide Y into primary rat brain cultures," Neuroscience Letters 1995; 190: 73-76.

Co-pending U.S. Appl. No. 11/178,978, inventors Fukumura, M., et al., filed Jul. 12, 2005 (Not Published).

H. Yoshiura, et al "Internet-Marks: Clear, secure and portable visual marks for cyber worlds", Lecture Notes in Computer Science, Springer Verlag, NY, vol. 1796, May 17, 2000, pp. 195-202.

De Fiebre, C.M. et al. "Differential Adenoassociated Virus Vector-Driven Expression of a Neuropeptide Y Gene in Primary Rat Brain Astroglial Cultures after Transfection with Sendai Virosomes Versus Lipofection™," *Neurochem. Res. 19*:643-648, Plenum Publishing Corporation (1994).

Kato, A. et al., "Initiation of Sendai virus multiplication from transfected cDNA or RNA with negative or positive sense," *Genes to Cells 1*:569-579, Blackwell Science Limited (1996).

Moriya, C. et al., "Large quantity production with extreme convenience of human SDF-1α and SDF-1β BY A Sendai virus vector," *FEBS Letts. 425*:105-111, Federation of European Biochemical Societies (1998).

Suzuki, J.-I. et al., "Prevention of graft coronary arteriosclerosis by antisense cdk2 kinase oligonucleotide," *Nature Med. 3*:900-903, Nature Publishing Group (1997).

Yamada, K. et al., "Efficient oligonucleotide delivery using the HVJ-liposome method in the central nervous system," *Am. J. Physiol. 271*:R1212-1220, American Physiological Society (1996).

U.S. Appl. No. 09/762,641, entitled "RNA Virus Vector with Contact Infiltration Capability," 30 pages (unpublished).

Office Action mailed Oct. 25, 1999, for U.S. Appl. No. 09/070,938, Nagai, Y., et al., filed Apr. 30, 1998.

Office Action mailed Feb. 16, 2000, for U.S. Appl. No. 09/070,938, Nagai, Y., et al., filed Apr. 30, 1998.

Office Action mailed Nov. 21, 2000, for U.S. Appl. No. 09/070,938, Nagai, Y., et al., filed Apr. 30, 1998.

Office Action mailed Dec. 6, 2001, for U.S. Appl. No. 09/070,938, Nagai, Y., et al., filed Apr. 30, 1998.

Office Action mailed Jan. 15, 2002, for U.S. Appl. No. 09/070,938, Nagai, Y., et al., filed Apr. 30, 1998.

Office Action mailed Jan. 13, 2003, for U.S. Appl. No. 09/070,938, Nagai, Y., et al., filed Apr. 30, 1998.

Office Action mailed Mar. 18, 1999, for U.S. Appl. No. 09/071,591, Nagai, Y., et al., filed May 1, 1998.

Office Action mailed Dec. 3, 1999, for U.S. Appl. No. 09/071,591, Nagai, Y., et al., filed May 1, 1998.

Office Action mailed Aug. 21, 2000, for U.S. Appl. No. 09/471,840, Nagai, Y., et al., filed Dec. 23, 1999.

Office Action mailed May 10, 2001, for U.S. Appl. No. 09/471,840, Nagai, Y., et al., filed Dec. 23, 1999.

Office Action mailed Dec. 6, 2001, for U.S. Appl. No. 09/471,840, Nagai, Y., et al., filed Dec. 23, 1999.

Office Action mailed Jan. 15, 2002, for U.S. Appl. No. 09/471,840, Nagai, Y., et al., filed Dec. 23, 1999.

Office Action mailed Jan. 13, 2003, for U.S. Appl. No. 09/471,840, Nagai, Y., et al., filed Dec. 23, 1999.

Office Action mailed Apr. 11, 2002, for U.S. Appl. No. 09/720,003, Akuta, T., et al., filed Sep. 4, 2001.

Office Action mailed Feb. 25, 2003, for U.S. Appl. No. 09/720,003, Akuta, T., et al., filed Sep. 4, 2001.

Office Action mailed Jan. 17, 2003, for U.S. Appl. No. 09/720,979, Fukumura, M., et al., filed Mar. 7, 2001.

Office Action mailed Jun. 8, 2004, for U.S. Appl. No. 09/720,979, Fukumura, M., et al., filed Mar. 7, 2001.

Office Action mailed Jan. 24, 2002, for U.S. Appl. No. 09/728,207, Nagai, Y., et al., filed Dec. 1, 2000.

Office Action mailed Oct. 18, 2002, for U.S. Appl. No. 09/728,207, Nagai, Y., et al., filed Dec. 1, 2000.

Office Action mailed Jul. 14, 2003, for U.S. Appl. No. 09/728,207, Nagai, Y., et al., filed Dec. 1, 2000.

Office Action mailed Nov. 4, 2003, for U.S. Appl. No. 09/728,207, Nagai, Y., et al., filed Dec. 1, 2000.

Office Action mailed Aug. 5, 2004, for U.S. Appl. No. 09/728,207, Nagai, Y., et al., filed Dec. 1, 2000.

* cited by examiner

A

B

Ischemia (+)

Ischemia (−)

SEQUENCE LISTING

```
<160> NUMBER OF SEQ ID NOS: 3

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 1
cggccgcaga tcttcacg                                              18

<210> SEQ ID NO 2
<211> LENGTH: 47
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 2
acttgcggcc gccaaagttc atctatgaag ttatgggatg tcgtggc              47

<210> SEQ ID NO 3
<211> LENGTH: 72
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 3
acttgcggcc gcgatgaact ttcaccctaa gtttttctta ctacggtcag atacatccac   60 acctttagc gg                                                      72
```

SENDAI VIRAL VECTORS COMPRISING FOREIGN GENES INSERTED BETWEEN THE R1 AND R2 LOCI

CROSS-REFERENCE TO RELATED APPLICATIONS

The present application is a continuation-in-part of U.S. patent application Ser. No. 09/720,979, filed Mar. 7, 2001, which is a 371 of International Patent Application No. PCT/JP99/03552, filed Jul. 1, 1999, which claims the benefit of Japanese Patent Application No. 10/204333, filed Jul. 3, 1998.

TECHNICAL FIELD

The present invention relates to a method of transferring a gene for gene therapy of nerve cells using a virus vector, more specifically, a negative-sense RNA virus vector.

BACKGROUND ART

Gene therapy for neurodegenerative diseases has tremendous potential, but its success will rely on the development of vectors that are safe and that stably or transiently express enough levels of therapeutic transgene. Therefore, it is an extremely important object in the gene therapy for humans and animals to develop a system whereby a gene is transferred into target organs and target cells with a high efficiency. Methods for transferring a gene include the calcium phosphate method, DEAE-dextran method, cationic liposome method, electroporation method, etc., and especially methods for transferring a gene in vivo include a method using virus or liposome, or a direct transfer method. Among them, the gene transfer performed using "a virus vector" obtained by recombination of viral gene is extremely useful for the transfer of a gene into cells, for example, for gene therapy because of easy transfer procedure and its high transfer efficiency.

Virus vectors commonly used at present in gene therapy include retrovirus vector, herpes simplex virus (HSV) vector, adenovirus vector, and adeno-associated virus (AAV) vector, etc. In particular, along with the recent progress in analysis of brain functions using MRI and PET, there has been an increased demand for vectors capable of efficiently infecting non-dividing nerve cells and mediating a high level transgene expression in the infected cells. Therefore, adenoviral vector, herpes simplex viral vector, AAV, HIV, etc. have received considerable attention.

Although HSV has been reported to be capable of transferring a gene into ganglions in the peripheral nervous system, a problem remains on the amount of its expression (Gene Therapy, 1995, 2: 209-217). HIV infection of nerve cells has also been confirmed (Nature Biotechnology, 1997, 15: 871-875). Since the chromosomal position into which the HIV genome is inserted is hardly predictable, there are possibilities of damaging a normal gene, activating a cancer gene, and inducing excessive or suppressed expression of a desired gene.

AAV has been used for the brain treatment in Parkinson's disease (Exp. Neurol., 1997, 144: 147-156) and mucopolysaccharidosis type VII (ASGT meeting, 1998, Abstract No. 692). However, there have been reported an incomplete transfer of the introduced gene into the substantia nigra in Parkinson's disease and its insufficient expression in the brain in mucopolyscchariclosis type VII.

Adenovirus has been most commonly used at present, and reported to be capable of transferring a gene into the pyramidal cell layer of hippocampus (Nature Medicine, 1997, 3: 997-1004). However, adenovirus has drawbacks, such as cytotoxicity and high immunogenicity.

On the other hand, since negative-sense RNA viruses, such as Sendai virus (hereinafter abbreviated as SeV), are not integrated into chromosomes, they do not activate cancer genes. Furthermore, since SeV is an RNA virus, it has advantages, such as protein expression in short time after infection and an extremely higher level expression of the transgene product compared with adenovirus.

GDNF is a neurotrophic factor that prevents dopaminergic neurons from dying and decreases dopamine-dependent behavioral deficits in rat and non-human primate models of Parkinson's disease (Bjorklund, A. et al. Neurobiol. Dis. 4: 186-200 (1997); Bowenkamp, K. E. et al., J. Comp. Neurol. 355: 479-489 (1995); Gash, D. M. et al., Nature 380: 252-255 (1996); Gash, D. M. et al., Ann. Neurol. 44: S121-S125 (1998); Hebert, M. A. and Gerhardt, G. A., J. Pharmacol. Exp. Ther. 282: 760-768 (1997)). However, in order for GDNF to be effective in a progressive neurodegenerative disease such as Parkinson's disease, chronically increased levels of GDNF near the dopaminergic neurons will most likely be needed. A recent study in Parkinson's patients infused intraventricularly with GDNF protein showed that GDNF protein did not penetrate the brain parenchyma to an appreciable extent (Kordower, J. H. et al., Ann. Neurol. 46: 419-424 (1999)). Gene delivery is the most promising approach for achieving chronically increased levels of GDNF near the dopamine neurons.

DISCLOSURE OF THE INVENTION

It is an objective of this invention to provide a method for transferring nucleic acid using a negative-sense RNA viral vector. This method is useful for gene therapy of nerve cells, etc.

The present inventors first prepared recombinant viruses carrying various foreign genes, using SeV, a typical negative-sense RNA virus and useful as a vector for gene therapy because of its safety and convenience. Subsequently, these recombinants were used to transfer the foreign genes into nerve cells, brain tissues, etc. As a result, the inventors found that the use of these recombinants enabled an efficient transfer of foreign genes into nerve cells and brain tissues. Furthermore, they found that the use of viral vectors of this invention led to high level expression of foreign genes introduced.

In addition, viral vectors of this invention transferred into the brain exhibited the limited proliferation. In other words, the expression of the vectors was reduced after a certain period of foreign gene expression. Furthermore, the gene therapy using a viral vector of this invention was applied to the brain of a β-glucuronidase-deficient mouse, which improved the symptoms of said mouse. Thus, the present inventors discovered that the viral vectors prepared could efficiently function in gene therapy of neuropathy where the therapy requires regulation of transgene expression.

The intraventricular administration of a viral vector of this invention carrying an FGF gene to gerbils or mice resulted in the vector infection of ependymal cells and the decrease of the food intake and body weight in the animals. Ependymal cells form a cell layer that separates the brain from ventricles, and in the third ventricle the cerebrospinal fluid and hypothalamic nuclei intimately interact. Since vectors of this invention can efficiently infect ependymal cells, they can be used to express a secretory protein in the ventricle so that the protein acts on hypothalamic nuclei (feeding center, satiety center, etc.). In addition, in an ischemic model using gerbils, it has been revealed that the cell injury is significantly reduced by introducing a viral vector for a growth factor expression into the hippocampus parenchymal cells, indicating a usefulness of the vector of this invention for preventing the cell death in brain ischemia. Furthermore, in an ischemic model using gerbil brain, it has been revealed that intraventricular administration of SeV expressing GDNF, a neurotrophic factor, significantly reduces cell loss accompanying ischemia. Neuroprotective effect of SeV administration into the lateral ventricle on one side is observed on the contralateral side as well as on the administered side. This indicates that the administered SeV or the expressed GDNF diffuses into the entire ventricle and that SeV can transfer a gene for therapy to neurons in wide area. These facts have indicated that vectors of this invention are useful as vectors for transfer of gene into the brain in various medical treatments.

The present invention relates to:

(1) a method for transferring nucleic acid into nerve cells, comprising a step of contacting the nerve cells with a negative-sense RNA viral vector or cells comprising said vector;

(2) a method of (1), wherein said nerve cells are central nervous system cells;

(3) a method of (2), wherein said central nervous system cells are ventricular ependymal cells;

(4) a method of (2), wherein said central nervous system cells are hippocampus cells;

(5) the method of (1), wherein nucleic acid contained in the negative-sense RNA viral vector comprises a foreign gene;

(6) a method of (5), further comprising allowing to transiently express said foreign gene;

(7) a method of (5), wherein said foreign gene encodes a secretory protein;

(8) a method of (7), wherein said protein acts on the hypothalamic nuclei;

(9) a method of (7), wherein said protein is capable of protecting the brain from ischemia;

(10) a method of (9), wherein said protein is neurotrophic factor;

(11) a method of (5), wherein said foreign gene is selected from the group consisting of FGF-1, FGF-2, FGF-5, NGF, CNTF, BDNF, GDNF, p35, CrmA, ILP, bcl-2 and ORF 150;

(12) a method for controlling the feeding behavior of animals, the method comprising administering a negative-sense RNA viral vector comprising FGF-1 or FGF-5 as a foreign gene to animals;

(13) a method for controlling the blood sugar level of animals, the method comprising administering a negative-sense RNA viral vector comprising FGF-1 or FGF-5 as a foreign gene to animals;

(14) the method of (1), wherein said negative-sense RNA virus belongs to the Paramyxoviridae family;

(15) a method of (14) wherein said virus belonging to the Paramyxoviridae family is Sendai virus; and

(16) a negative-sense RNA viral vector used for transferring nucleic acid into nerve cells by the method of (1).

In this invention, "negative-sense RNA viral vectors" include a complex that is derived from a negative-sense RNA virus and has the infectivity. Herein, "infectivity" means the "capability of a complex to transfer its nucleic acid or other substances inside thereof into a cell through its ability to adhere and fuse to the cell membrane".

In this invention, a negative-sense RNA viral vector can be prepared by using, for example, a negative-sense RNA virus as a starting material. Viruses used as starting materials are exemplified by, for example, viruses belonging to the Paramyxoviridae such as SeV, Newcastle disease virus, mumps virus, measles virus, RS virus (Respiratory syncytial virus), rinderpest virus and distemper virus; viruses belonging to the Orthomyxoviridae such as influenza virus; viruses belonging to the Rhabdoviridae such as vesicular stomatitis virus and rabies virus; etc.

When SeV is used, a group of proteins encoded by three genes, NP, P/C and L, which are thought to be essential for its autonomous replication, are not necessarily required to be encoded by the viral vectors of this invention. For example, the vector of this invention can be produced in the host cells that carry the genes encoding this group of proteins so that these proteins are provided by the host cells. In addition, the amino acid sequences of these proteins are not necessarily identical to those native to the virus. Any mutations can be introduced, or substitutions by homologous genes from other viruses can be used as long as their nucleic acid-transferring activities are equal to or higher than those of the naturally occurring proteins.

Further, when SeV is used, a group of proteins encoded by the M, F and HN genes, which are thought to be essential for the disseminative capability of the virus, are not necessarily required to be encoded by the viral vectors of this invention. For example, the vector of this invention can be produced in the host cells that carry the genes encoding this group of proteins so that these proteins are provided by the host cells. In addition, the amino acid sequences of these proteins are not necessarily identical to those are native to the virus. Any mutations can be introduced into the genes or substitution of the genes by homologous gene from other virus can be used as long as their nucleic acid transferring activities are equal to or higher than that of the naturally occurring proteins.

To transfer a foreign gene into nerve cells, a complex comprising a recombinant viral genome into which a foreign gene is inserted can be prepared and used. The complex comprising a recombinant viral genome can be obtained by means of in vitro or in vivo transcription of a modified cDNA derived from any of the aforementioned viruses or a recombinant virus thereof followed by reconstitution of the virus. A method for reconstituting a virus has already been developed (see WO97/16539).

In addition, instead of the complete SeV genome, incomplete viruses such as defective interfering particles (DI particles) (J. Virol. 68, 8413-8417, 1994), synthetic oligonucleotides, etc. may also be used as the component to constitute the complex.

When SeV is used as a material, a complex may contain all the three genes, M, F and HN, which are involved in the disseminative capability of the virus. However, in general, even though a complex comprising all the M, F and HN genes is transferred into the brain, the complex presumably fails to exhibit disseminative capability after formation of the viral particles, because of the absence of protease to cleave F protein, a protein essential for the disseminative capability of SeV. Herein, "disseminative capability" means "the capability to form infectious particles or their equivalent complexes and to disseminate them to other cells following the transfer of nucleic acid into host cells by infection or artificial techniques and the intracellular replication of the nucleic acid". However, to increase the safety, the genes involved in the disseminative capability of the virus are preferably eliminated or functionally inactivated in the viral genome in the complex. In the case of SeV, genes involved in the disseminative capability of the virus are the M, F and/or HN genes. A reconstitution system of such complexes has been developed (WO97/16538). For example, for SeV, a viral vector comprising a genome from which the F and/or HN genes are deleted can be prepared. Such vectors are also included in the vectors of this invention for transferring nucleic acid into nerve cells.

The complex may contain on its envelope surface a factor that is capable of adhering to a specific cell, such as an adhesion factor, ligand, receptor, etc. For example, parts of the genes of a recombinant negative-sense RNA virus can be modified to inactivate the genes related to immunogenicity or to enhance the efficiencies of transcription and replication of RNA.

RNA contained in the complex can incorporate a foreign gene at its appropriate site. To express a desired protein, a foreign gene encoding the protein is incorporated into the RNA. For the SeV RNA, a nucleotide sequence consisting of nucleotides in multiples of six is desirably inserted between the R1 and R2 sequences (Journal of Virology, 1993, Vol. 67, No. 8, pp. 4822-4830). Expression of the foreign gene inserted into the RNA can be regulated via the insertion site of the gene or the RNA sequence in the vicinity of the inserted gene. For example, in the case of SeV RNA, it is known that the nearer to the NP gene the insertion position of the RNA comes, the higher the expression level of the inserted gene becomes.

A foreign gene encoded by the RNA contained in the complex can be expressed by infecting cells with the complex. As shown in the examples below, it has been demonstrated that a complex prepared as one embodiment of this invention by using the reconstitution system of SeV enables an efficient transfer of a foreign gene into various nerve cell strains. As shown in Example 5, it has also been revealed that another embodiment of the complex of this invention in which the β-glucuronidase gene is used as a foreign gene shows a significantly higher expression level than retroviral vectors. Owing to these characteristics, the complex of this invention can be used for transferring genes into nerve cells. Since, one embodiment of the complex of this invention shown in Example 6 decreases its expression about one week after the intraventricular administration, it is useful in such a gene therapy that requires the gene expression of only for a limited period of time.

Nucleic acid or other compounds contained in the complex prepared can be introduced into nerve cells by contacting the complex with nerve cells or by directly contacting the viral vector-producing cells with nerve cells. When the complex is administered into the brain, the administration can be performed, for example, by boring a hole on the cranial bone after craniotomy under anesthesia, followed by injecting the complex using a glass needle or the like material. The complex can contain foreign genes. Foreign genes may include any types of genes, such as the nerve cell-specific gene, apoptosis-suppressing gene, other genes for treating various type of diseases, etc. Such genes can take the forms of antisense DNA and ribozyme so as to inhibit the function of a specific gene.

For example, it has been revealed that the brain cell death in ischemic tissues does not occur soon after ischemia, but within several days after that (Neurosci. Lett. 1998, 240: 69-72). To prevent the brain cell death in such a case, a complex of this invention comprising a gene responsible for suppression of the cell death, such as bcl-2, etc. can be used. In fact, during the investigation whether administration of the vector of this invention could prevent the delayed loss of fragile nerve cells due to depletion of nutrients caused by ischemia, it was revealed that administration of an FGF-1 expression vector could significantly prevent the cell loss (Example 10). In addition, as demonstrated in Examples 6 and 8, the complex of this invention can transfer a foreign gene into ependymal cells and cells present along the ventricles via intraventricular administration. In fact, it was demonstrated that intraventricular administration of a GDNF expression SeV vector enabled efficiently transferring a gene to central nerves containing hippocampus CA1 region and strongly reduced nerve cell death caused by ischemia (Example 11). Use of a gene expressing a secretory protein as a foreign gene can diffuse the protein through the spinal fluid into the brain including the hippocampal area. As shown in Example 7, it is also possible to express a foreign gene in the pyramidal cells of the hippocampus by administration of a complex of this invention. As shown in Examples 6 and 7, one embodiment of the complex of this invention was expressed in nerve cells of hippocampus even 13 days after the administration of the complex into the brain. The transfer of the complex did not cause cell death. These results indicate the usefulness of the complex of this invention for the gene therapy of central nerves. For example, in Example 9, it was demonstrated that the intraventricular administration of an FGF expression vector could successfully control the amount of food intake and reduce the body weight. Body weight loss attributable to FGF-2 (Denton, D. A. etal. (1995) Physiol. Behav. 57 (4): 747-752) and reduction of the blood sugar level accompanied with the body weight loss (Stephens, T. W. et al. (1995) Nature 377 (6549): 430-532) were already reported, which coinsides with the results obtained in the present invention that the blood sugar level was reduced associated with the body weight loss.

Thus, the vectors of this invention provide a novel mode of vector administration targeting ependymal cells. In addition to ependymal cells, target cells include, but not limited to, cells present along the ventricles, cells in the hippocampal region, especially hippocampus pyramidal cells, neural stem cells, neural crest cells derived from mammalian embryos, etc. With the vector of the present invention encoding a protein having nerve cell-protective effects, the protein can be expressed in target nerve cells or their surrounding cells and the cells can be protected from neurodegeneration occurring in diseases and injury. In particular, the vector of the present invention can be applied to Parkinson's disease, ischemia, etc. There is no limitation on administration route to central nervous system, but administration via cerebral ventricle is preferable. The present invention particularly provides a method for transferring nucleic acid into central nervous system cells, the method comprising a step of contacting the central nervous system cells with a negative-sense RNA viral vector or cells comprising the vector by administration of the vector via cerebral ventricle. Herein, administration of a vector via cerebral ventricle means a method for administration of a vector, the method comprising a step of diffusing the vector into the cerebral ventricle. Examples of the administration include intraventricular administration, intraspinal administration, etc. Thus, a desired gene can be transferred to nerve cells in wide area along cerebral ventricule containing the vicinity of hippocampus. Genes that can be introduced include, but not limited to, those for fibroblast growth factors, nerve growth factors, apoptosis inhibitors, heat shock proteins, peroxidases, neurotrophic factors, etc. Specific examples of such genes include those for FGF-1 (J. Biol. Chem. 271 (47): 30263-30271, 1996), FGF-2 (Yoshimura, S. etal., Proc. Natl. Acad. Sci., Apr.24, 2001, 10.1073/pnas.101034998),FGF-5

(Proc. Natl. Acad. Sci. U.S.A. 87 (20): 8022-8026, 1990), NGF (Nature, 302 (2): 538-540, 1983), CNTF (Nature, 357 (6): 502-504, 1992), BDNF (EMBO J., 9 (8): 2459-2464, 1990; Genomics, 10 (3): 558-568, 1991), GDNF (J. Neurosci. Res. 41 (2): 279-290, 1995), p35 (J. Virol. 61 (7): 2264-2272, 1987), CrmA (Proc. Natl. Acad. Sci. U.S.A. 83: 7698-7702, 1986), ILP (EMBO J., 15 (11): 2685-2694, 1996), bcl-2 (Oncogene., 4 (11): 1331-6, 1989), ORP 150 (Biochem. Biophys. Res. Commun. 230 (1): 94-99, 1997), etc. For example, the present invention provides a method for suppressing neurodegeneration, the method comprising administering a negative-sense RNA viral vector comprising GDNF as a foreign gene to animals. Examples of neurodegeneration to which the method can be applied include, in particular, those accompanying ischemic cell loss. Vectors of this invention are useful for not only searching genes by using DNA chips and DNA arrays, but also conveniently preparing model mice as well as developing medicines.

Animals into which the complex of this invention can be introduced include all kinds of mammals such as human, gerbil, mouse, rat, rabbit, cattle, monkey, etc.

BEST MODE FOR CARRYING OUT THE INVENTION

The present invention will be explained in detail with reference to examples below, but is not to be construed as being limited thereto. Any patents, patent applications, and publications cited herein are incorporated by reference.

EXAMPLE 1

Preparation of the Replication Competent SeV

Figure 1:
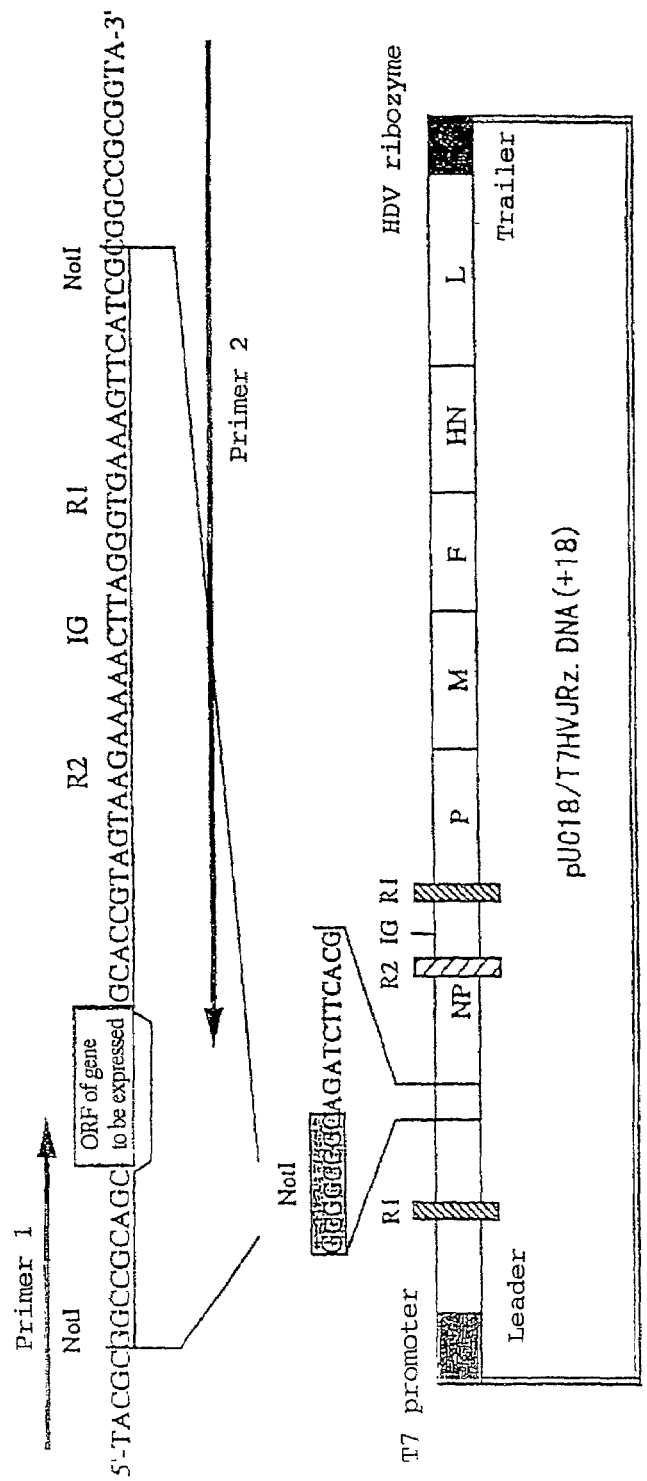
FIG. 1 schematically shows a method for constructing the replication competent seV comprising a foreign gene, such as for GFP or β-glucuronidase. Using primer 1, which has a NotI site, and primer 2, which comprises, a transcription termination signal (R2), an intervening sequence (IG), a transcription initiation sequence (R1) and a NotI site, the ORP of a foreign gene is amplified by PCR so that the ORF is placed between SEQ ID NOs: 1 and 2, and an amplified fragment is inserted into the NotI site (SEQ ID NO: 3) of pUC18/T7HVJRz.DNA (+18).

A NotI fragment comprising a foreign gene to be transferred, transcription initiation (R1) and termination (R2) signals, and intervening sequence (IG) (FIG. 1) was amplified by PCR and inserted into the NotI cleavage site of SeV transcription unit pUC18/T7HVJRz. DNA (+18) (Genes Cells, 1996, 1: 569-579) (FIG. 1). According to an established method (Genes Cells, 1996, 1: 569-579),using LLCMK2 cells and embryonated chicken eggs, the virus comprising the above-described genes was reconstituted, resulting in the recovery of the virus comprising the desired gene.

EXAMPLE 2

Confirmation of Infectivity of "GFP/SeV" to Established Nerve Cell Lines

As the established cell lines, rat phenochromocytoma cells (PC12) human neuroblastoma cells (IMR-32) and human glioblastoma cells (A172) were used. PC12 cells were cultured in a DMEM supplemented with horse serum and calf serum to a final concentration of 5% for each serum. To promote neurite outgrowth, a nerve growth factor (NGF7S) was added to the medium to a final concentration of 50 ng/ml. An MEM containing 10% calf serum supplemented with an MEM sodium pyruvate solution and MEM non-essential amino acid solution to the final concentrations of 1 mM and 0.1 mM, respectively, was used for the culture of human neuroblastoma cells (IMR-32). Human glioblastoma cells (A172) were cultured in a MEM (a high glucose medium) containing 10% calf serum.

$10^5$ cells were plated into a 6-cm dish containing NGF in the medium, incubated for 3 days to induce the neurite outgrowth and then used for PC12 cell infection experiment. After removing the medium, the cells were washed once with PBS. SeV into which a GFP gene is introduced (hereinafter referred to as GFP/SeV vector) was diluted with 500 μl of PBS supplemented with 1% bovine serum albumin to $10^6$ plaque forming unit (p.f.u.), and was added to the cells to infect GFP/SeV vector for 20 min under the conditions where the cells were protected from drying. After the infection, the medium (5 ml) was added to the plates, and the cells were cultured for 2 days. After culturing, the cells were examined for GFP fluorescence under a fluorescence stereoscopic microscope. As a result, the infection of PC12 cells with GFP/SeV vector was confirmed by the GFP fluorescence within the cells. Fluorescence emission could not be observed with the control cells infected with SeV carrying no GFP gene and non-infected cells.

IMR-32 cells ($3\times10^5$ cells) were plated into a 10-cm plate containing the above-mentioned medium, and cultured overnight. Based on the cell number estimated to be $6\times10^5$ after the culture, GFP/SeV vector was diluted to m.o.i. (multiplicity of infection) of 10 with 1000 µl of PBS containing 1% bovine serum albumin. After the cells were infected with the virus for 20 min, they were cultured in the medium for 12 or 36 h, and then examined for the GFP fluorescence under a fluorescence stereoscopic microscope. After the culture for 12 h, fluorescence was observed in the cell body of GFP/SeV-infected cells. After the 36-h culture, GFP fluorescence was observed in the neurite portion in addition to the cell body. Fluorescence was not observed in the control cells infected with SeV carrying no GFP gene as well as non-infected cells.

A172 cells were also infected with the virus in a similar manner as that used for IMR-32 cells. Fluorescence was observed in the cell body of GFP/SeV-infected cells, but not in the control cells infected with Sev carrying no GFP gene as well as non-infected cells.

GFP/SeV vector infected all the established nerve cell strains used in the present study, and succeeded in expressing GFP from the GFP gene within the cells. These results indicated a possibility of the SeV infection of the primary culture of brain cells and of brain cells by in vivo administration of the virus.

EXAMPLE 3

Culture of the Primary Rat Brain Cells

An SD rat of 18-day pregnancy was deeply anesthetized with diethyl ether, and euthanized by the exsanguination from the axillary artery. After the abdominal region was disinfected with 95% ethanol, it was subjected to laparotomy to remove the fetuses together with the womb. Subsequent procedures were all performed under the germ free conditions on ice, or in ice-cold solutions unless otherwise stated. Fetuses was removed from the womb using scissors and roundheaded forceps, and transferred to a plate containing 20 ml of an operation solution (50% DMEM and 50% PBS). After the fetuses were placed on a sterilized gauze pad, their scalp and skull were incised along the midline using two pairs of INOX#4 forceps. Subsequently, a pair of INOX#7 forceps was inserted along the undersurface of the brain tissue to scoop up the brain tissue as a whole with the medulla oblongata being cut off, and the tissue was excised and placed in the operation solution. Under a stereoscopic microscope, the brain in the operation solution was filleted into three portions using two scalpels to separate the brain stem, and two pieces of cerebral hemispheres containing the hippocampus and corpus striatum were transferred into another operation solution with roundheaded forceps. Under a stereoscopic microscope, the meninx was completely removed from the surface of the brain tissue using two pairs of INOX#5 forceps, and transferred into another operation solution using roundheaded forceps for washing. Six pieces of cerebral hemispheres were placed into a preservation solution (90% DMEM (containing 5% horse serum and 5% calf serum), and 10% DMSO) with roundheaded forceps, and then they were cut into small pieces less than 1 mm using a scalpel on slides. The tissue pieces thus cut were placed into about 1.5 ml of the preservation solution in a pre-cooled tube, which was stored in a freezing container, frozen slowly over a period of 3 hours, and then stored in liquid nitrogen. The tissue pieces of 6 cerebral hemispheres were taken out from the liquid nitrogen, thawed at 320° C., washed twice in 8 ml of the operation solution, and allowed to stand for 30 sec, and then the supernatant was removed. To the tissue pieces were added 5 ml of an ice-cold papain solution (papain 1.5 U, cysteine 0.2 mg, bovine serum albumin 0.2 mg, glucose 5 mg, and DNase 0.1 mg/ml) which had been filtered and sterilized. The mixture was warmed at 32° C. for 15 min and mixed by inverting the tube every 5 min. The supernatant was separated, and 5 ml of a solution containing 20% calf serum were added. A papain solution (5 ml) preheated to 32° C. was added to the precipitate fraction, and the resulting mixture was further warmed for 15 min. The mixture was mixed by inverting the tube every 5 minutes. After good turbidity of the supernatant as well as translucence of the tissue pieces were confirmed, the tissue pieces were split by pipetting. The first supernatant fraction preheated to 32° C. was added to this sample solution, and the resulting mixture was centrifuged in a centrifuge preheated to 32° C. (at 1200 rpm for 5 min). After removal of the supernatant, 5 ml of DMEM (containing 5% horse serum and 5% calf serum) were added to and mixed with the residue to break the cells up, followed by centrifugation under the above-described conditions. After the removal of supernatant, 2 ml of DMEM (containing 5% horse serum and 5% calf serum) were added to the residue, and the resulting mixture was stirred. As a result of cell counting, the cell number was found to be $5\times10^6$ cells/ml. The primary culture of brain cells thus obtained were seeded on a polyethylene imine-coated plate and cultured.

EXAMPLE 4

Confirmation of Infectivity of SeV to the Primary Culture of Brain Cells Using GFP/SeV Vector The primary culture of brain cells obtained in Example 3 was cultured in a 10-cm plate for 3 days. After the removal of the supernatant, a sample solution prepared by diluting GFP/SeV vector in 1000 µl of PBS containing 1% bovine serum albumin was added to the culture to infect with the virus for 20 min. After the infection, 10 ml of DMEM medium (containing 5% horse serum and 5% calf serum) was added, and the cells were cultured for 2 days. The cells were then examined for the fluorescence of GFP under a fluorescence stereoscopic microscope. Almost all the cells displayed fluorescence. That is, it was confirmed that SeV infects even the primary culture of brain cells.

EXAMPLE 5

Infection of SeV Vector Carrying the β-glucuronidase Gene (Hereinafter Abbreviated as β-glu/Sev) to Human Fibroblast Cells Deficient of the β-glucuronidase Gene and Expression of Said Enzyme in the Cells For the implementation of this invention, human fibroblast cells deficient of the β-glucuronidase gene (hereinafter abbreviated as β-glu-deficient cell) and human normal fibroblast cells were used.

Mucopolysaccharidosis type VII, one type of mucopolysaccharidosis, is caused by deficiency of β-glucuronidase, and shows a variety of clinical symptoms ranging from a mild case to severe case with fetal hydrops. There are many severe cases showing various symptoms developed during the infantile period, including characteristic facial feature, splenohepatomegary, psychcomotor retardation, bone deformation, etc.

It has been indicated that, for the intracellular transport of β-glucuronidase to lysosome, the addition of sugar chain to the enzyme molecule and the phosphorylation of the 6-position of the mannose moiety of the enzyme are necessary. On the arrival at lysosome, C-terminus of the enzyme undergoes proteolysis.

Prior to the implementation of this invention, β-glu/SeV vector was examined for 1) its infectivity to human fibroblast cells, 2) its expression amount, and 3) the presence of its molecular species to be transported to lysosome.

1) β-glu deficient fibroblast cells were prepared so that $10^5$ cells/well were placed in a 6-well plate. β-glu/SeV vector was diluted in 100 μl of PBS containing 1% bovine serum albumin so that the multiplicity of infection (m.o.i.) became 5, and the overnight-cultured β-glu deficient cells were infected for 1 h. The cells were cultured in a serum-free MEM for 24 h. The cells thus cultured were fixed in a mixture of formalin and acetone (1:7, v/v). With naphthol AS-BI glucuronide as a substrate, the reaction was performed in the acetate buffer, pH 5.0, at 37° C., and the substrate decomposition was monitored by the red coloration. As a result, the cytoplasm of β-glu deficient cells incubated with "β-glu/SeV" was stained red, indicating that β-glu deficient cells were infected with "β-glu/SeV" to express the transferred gene.

2) β-glu deficient cells were prepared so that $10^5$ cells/well were placed in a 6-well plate. "β-glu/SeV" was diluted in 100 μl of PBS containing 1% bovine serum albumin so that the multiplicity of infection (m.o.i.) became 0.1 and 1.0, and incubated with overnight-cultured β-glu deficient cells for 1 h. The cells were cultured in a serum-free MEM for 24 or 48 h. After the incubation, cells were recovered and sonicated to prepare intracellular fractions. With 4-methylumbelliferyl-β-D-glucuronide as a substrate, the amount of 4-methylumbelliferone (MU), the enzymatic reaction product, was determined by measuring the fluorescence intensity with a fluorospectrophotometer. The results are shown in Table 1. In this table, the expression amount was represented by the amount of 4-methylumbelliferone (MU) produced by 1 mg of protein in the intracellular fraction in 1 h.

TABLE 1

| Cell | Infecting condition | Amount of expression (nmol MU/mg total protein/h) |
| --- | --- | --- |
| β-glu-deficient fibroblast | No infection | 53 |
| Normal fibroblast | No infection | 276 |
| β-glu-deficient fibroblast | β-glu/retro | 911 |
| β-glu-deficient fibroblast | β-glu/SeV (m.o.i. = 0.1, 24 h) | 15,900 |
| β-glu-deficient fibroblast | β-glu/SeV (m.o.i. = 1.0, 24 h) | 27,100 |
| β-glu-deficient fibroblast | β-glu/Sev (m.o.i. = 0.1, 48 h) | 21,100 |
| β-glu-deficient fibroblast | β-glu/Sev (m.o.i. = 1.0, 48 h) | 32,300 |

As shown in Table 1, the expression amount ranged 15,900-32,300 (nmol MU/mg total protein/h), and 276 for normal fibroblast cells and 911 for the cell expressingβ-glucuronidase with a retrovirus vector (β-glu/retro), indicating that SeV strongly expresses a transgene in the SeV-infected cells.

3) The fractions obtained in 2) were used as the intracellular fraction of "β-glu/SeV"-infected-β-glucuronidase-deficient-fibroblast cells. As the culture supernatant fraction, proteins contained in the culture supernatant were recovered by precipitation with cold acetone. Test samples thus obtained were subjected to Western blot analysis using an anti-human β-glucuronidase antibody. As a result, in the intracellular fraction of "β-glu/SeV"-infected-β-glucuronidase-deficient-fibroblast cells, two types of proteins were identified; one has high molecular weight and another has low molecular weight, and both are reactive with the anti-human β-glucuronidase antibody. The band of the low molecular weight protein corresponds to that of the protein reactive with the anti-human β-glucuronidase antibody in normal fibroblast cells, indicating that it is a molecular species of β-glucuronidase the C-terminus of which has undergone pro-teolysis after transported to lysosome. The high molecular weight protein was not observed in the normal fibroblast cells, but present in the intracellular and supernatant fractions of β-glu/SeV-infected-β-glucuronidase-deficient fibroblast cells. The supernatant fraction contained only the high molecular weight protein. This may be due to too high an expression of β-glucuronidase caused by β-glu/Sev vector infection, in which transport of the high molecular weight protein species to lysosome failed to catch up with such a high enzyme expression, resulting in the secretion of the protein into microsomes or extracellular space. Alternatively, judging from its molecular weight, the high molecular weight protein may be a molecular species with a sugar chain attached but without the 6-position of mannnose moiety being phosphorylated so that it cannot be transported to lysosome.

Thus, the human β-glucuronidase, which is assumed to be transported to lysosome, was able to be expressed in the intracellular fraction of β-glu/SeV-infected-β-glucuronidase-deficient-fibroblast cells.

EXAMPLE 6

Figure 2:
FIG. 2 is a frontal cross sectional view of the mouse brain showing the expression of GFP in a mouse infected with SeV vector comprising the GFP gene (GFP/SeV).

Expression of GFP in Ependymal Cells by Intraventricular Administration of GFP/SeV Mice of 8-10 weeks old were anesthetized with 200 μl of 10-fold diluted Nembutal. After craniotomy, a hole of 1 mm in diameter was made in the skull at the position 1.0 mm from the bregma and 1.5 mm to the right of the midline with a dental drill. After the removal of the dura, GFP/SeV vector was administered at the position 1.3 mm deep using a 27 G syringe needle. The dose of GFP/SeV vector was 20 to 30 μl, and the number of the virus contained in the sample solution was estimated $1 \times 10^7$ p.f.u. to $1.5 \times 10^7$ p.f.u. Control mice were administered PBS or SeV carrying no GFP gene. Autopsy was performed 3, 5, 7 and 10 days after the administration. A whole brain was removed, and a frontal cross section was made. Under a stereoscopic fluorescence microscope, GFP fluorescence was observed. In the dissected brain autopsyed 3 days after the administration of GFP/SeV vector, the conspicuous GFP fluorescence was observed. At the site along the ventricle of the frontal cross section, distinct fluorescence of GFP was observed (FIG. 2). As described in Example 8 below, SeV-infected cells emitting GFP fluorescence were thought to be ependymal cells. The cells along the lateral ventricle also became fluorescent 5 and 7 days after the infection. However, the fluorescence intensity was significantly decreased in the cells 7 days after the infection, and no fluorescent brain cells could be observed 10 days later. Fluorescence could not be observed in the control mouse brains to which PBS or SeV carrying no GFP gene had been administered as a control.

EXAMPLE 7

Administration of GFP/SeV Vector to Brain Parenchyma Under Stereotaxy

To examine the SeV infection of nerve cells, especially pyramidal cells of hippocampus, which is the main object of this invention, precisely targeted administration of SeV to the vicinity of hippocampus is required. Therefore, a stereotaxy was conducted to introduce SeV into the brain parenchyma and the brain parenchymal cells were examined for the infection. As the experimental animals, 1) mouse and 2) rat were used.

1) Two holes of 1 mm in diameter each were made through the skull at the position 2 mm to the left and right of the medline and 3 mm anterior to the bregma using a dental drill. GFP/SeV vector (1.5 µl each) was administered to the parenchymal portions, 3.5 mm deep on the right side and 2.5 mm deep on the left side, using a glass capillary. The skull was closed, and surgically opened 3 days later to examine the GFP expression, which was observed in the parenchymal portion. After the fixation with ethanol, frozen tissue slices were prepared. Although GFP fluorescence was significantly reduced in the frozen slices after ethanol fixation due to the outflow of chromophores, fluorescent sites were still observed. In the white matter near the internal capsule, GFP fluorescence was observed on the axon from which myelin protein was eluted with ethanol. Furthermore, GFP fluorescence was also observed in the axon in the area presumed to be the corpus striatum.

These results demonstrated that GFP/SeV vector was capable of infecting nerve cells of the mouse brain.

2) Since a precise stereograph has already been made for rat, GFP/SeV vector can be accurately administered to the vicinity of pyramidal cells in the hippocampus CA1 area. A rat weighing about 170 g was anesthetized, and, after craniotomy, two holes of 1 mm in diameter each were made through the skull at the positions 2 mm to the left and right of the medline and 4.5 mm anterior to the internal (lambda) with a dental drill. GFP/SeV vector (1.5 µl each) was administered to the parenchymal portions, 3.5 mm deep on the right side and 2.5 mm deep on the left side, using a glass capillary. The skull was closed, and surgically opened 3 days later to examine the GFP expression. As a result, the GFP expression was observed in the hippocampus CA1 pyramidal cell area, where GFP/SeV vector was administered in 2.5 mm deep. Enlarged view of the region adjacent to the hippocampus by fluorescence microscopy revealed the marked fluorescence in the cell bodies of the hippocampus CA1 pyramidal cells and dendrites. The GFP expression was observed even in the pyramidal cells 13 days after the administration. Even 13 days after the administration of GFP/SeV, the GFP expression was observed in the cell bodies and dendrites of the pyramidal cells. These results demonstrate that SeV infection does not cause the nerve cell death even 13 days after the infection, strongly suggesting the usefulness of SeV as a vector for the gene therapy directed to prevention of the cell death following the brain ischemia.

EXAMPLE 8

Gene Therapy Trial on β-glucuronidase-deficient Mice Using β-Glu/SeV Vector

The results of Example 6 indicate that the ependymal cells are infected with SeV by intraventricular administration. Therefore, the inventors conducted an experiment in which β-glu/Sev vector is administered to β-glucuronidase-deficient mice (J. Clin. Invest., 1989, 83: 1258-1266) to induce secretion of β-glucuronidase from the infected cells into the cerebrospinal fluid and then to be taken up by target cells so that the symptoms would be improved.

Figure 3:
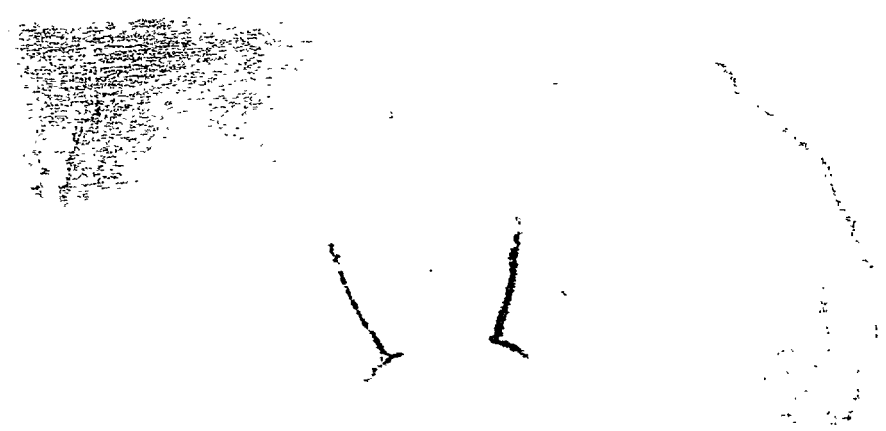
FIG. 3 is a cross sectional view of the lateral ventricle showing the expression of β-glucuronidase in a β-glucuronidase-deficient mouse 3 days after the infection with SeV vector carrying the β-glucuronidase gene.
Figure 4:
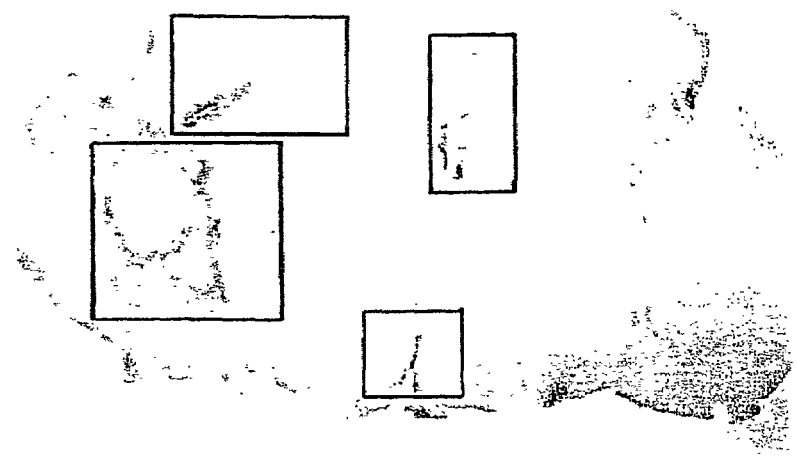
FIG. 4A shows a cross sectional view of the lateral ventricle showing the β-glucuronidase expression (framed areas) in the ventricle of a β-glucuronidase-deficient mouse 12 days after the infection with SeV vector carrying the β-glucuronidase gene.
FIG. 4B shows the section adjacent to that of FIG. 4A stained by Lorbacher method.
Figure 4:
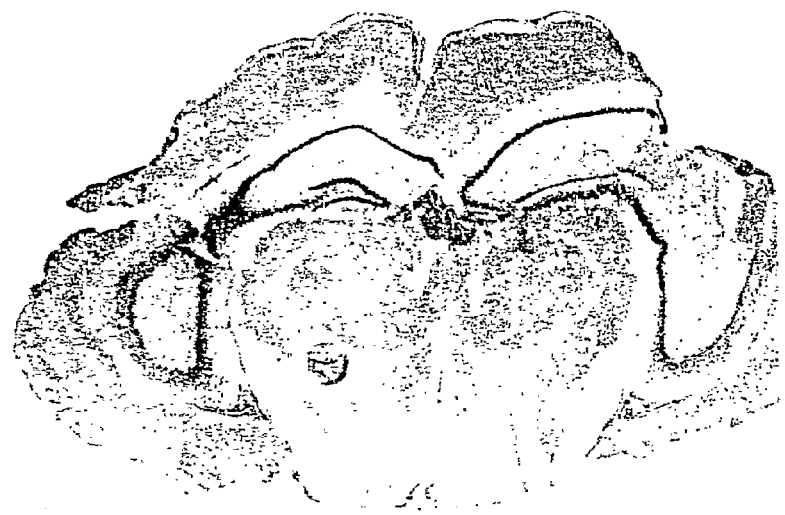

Homozygous mice were selected from mice obtained by breeding heterozygous mice based on the β-glucuronidase activity in the tail vein blood of the mice and on the presence of the N1aIV cleavage site in the PCR amplification fragments of the β-glucuronidase gene-deficient site on the chromosomes of the mice, and were used in the present experiment. Administration of β-glu/SeV vector was carried out according to the method described in Example 6. The brain was excised 3 or 12 days after the administration to prepare the frozen tissue slices. The β-glucuronidase activity in the tissue was assayed using a modification of the method described in Example 5, 1). As shown in FIG. 3, the sites at which β-glucuronidase was expressed were strongly stained red along the ventricles. When magnified by microscopy, the ependymal cells of the lateral ventricle were verified to strongly express β-glucuronidase, which was then secreted from the cells. On the tissue slice prepared 12 days after the administration (FIG. 4), βglucuronidase that had been expressed in and then secreted from the ependymal cells of the lateral ventricle was shown to be diffused into the ventricle with the migration of the spinal fluid to reach the vicinity of the hippocampus. Physical capabilities of the homozygous mice was apparently improved, although slightly, by this administration.

EXAMPLE 9

Experiments on Eating Depression Caused by Administration of the Sendai Viral Vector Carrying FGF-1 or -5 (Eating Depression Experiments in Gerbils and Mice)

Figure 5:
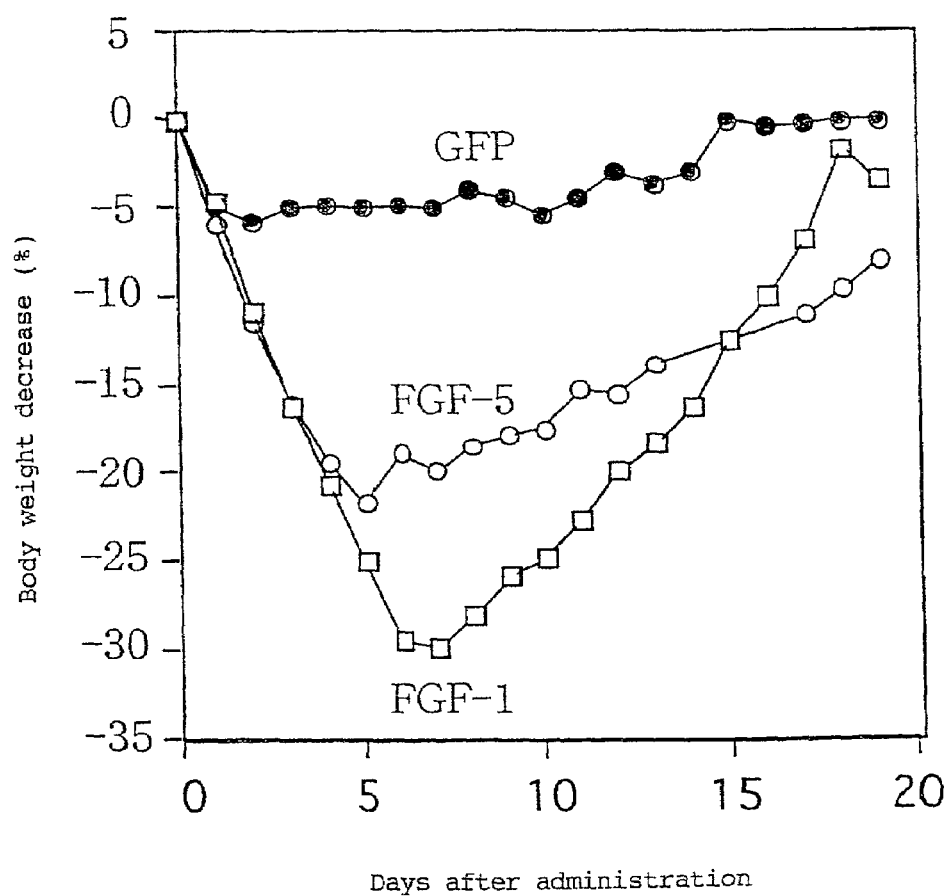
FIG. 5 is a graph showing changes in the body weight of gerbils after the intraventricular administration of SeV vector expressing FGF-1, FGF-5 and GFP.

Gerbils (weighing 60 to 80 g) were anesthetized with Nembutal, fixed onto a stereotaxic instrument, depilated, and then incised in the scalp along the medline. A hole was made in the skull at the position 1.0 mm from the bregma and 1.5 mm to the right of the medline using a dental drill with care to avoid damaging the blood vessels under the cranial bone. After drilling the hole, the dura and such were removed with tweezers. Mouse FGF-1/SeV vector ($5 \times 10^6$ pfu), human FGF-5/SeV vector ($1 \times 10^7$ pfu) and GFP/SeV vector ($5 \times 10^6$ pfu) were injected 1.0 mm deep into the right lateral ventricle (n=2) with a 30G syringe needle. The recombinant viruses were prepared according to Example 1. Changes in the body weight were monitored by measuring the weight, and decrease in the body weight was observed from the day after the administration (FIG. 5). In the FGF-1-administered group, the body weight started to decrease from the day after the administration, and continued to decrease by about 5% everyday till day 5, resulting in a 29.5% decrease on day 6, and the maximum decrease of 29.8% was observed on day 7. Then, the body weight turned to increase, and was recovered to a 3.5% decrease 20 days after the administration. In the FGF-5 administered group, the body weight started to decrease from the next day, reached the maximum of 21.7% decrease 5 days after the administration, and then turned to increase, being recovered to a 8.0% decrease on day 20. In the FGF-9 administered group, similar decrease in the body weight was observed from the next day, showed the maximum of 22.9% 5 days after the administration, and then turned to increase, being recovered to a 6.40% decrease on day 20. In the control group to which GFP/SeV was administered, the maximum of a 5.8% decrease in the body weight, which was presumably caused by the administration itself, was observed. However, the rate of the body weight loss was relatively small as compared with the FGF-administered groups, clearly indicating that FGF affects the body weight loss.

Since the body weight decrease due to the administration of FGF-1/SeV vector and FGF-5/SeV vector was observed in gerbils, more-detailed study was performed using B-6 mice (weighing about 20-22 g) The right lateral ventricle was selected as the administration site, and a hole of 1.0 mm in diameter was made in the skull at the position 1.0 mm from the bregma and 1.5 mm to the right of the medline with a dental drill. After the removal of the dura, a sample was administered to the animal in the hole at the depth of 1.3 mm with a 27G-syringe needle. The sample solutions were prepared by adding 9 µl, 8 µl and 9 µl of PBS to 1 µl of FGF-1/SeV vector ($1\times10^6$ pfu), 2 µl of FGF-5/SeV vector ($2\times10^6$ pfu), and 1 µl of control GFP/SeV vector ($1\times10^6$ pfu) solutions, respectively. The body weight and the food intake were monitored for 2 weeks after the viral administration.

Figure 6:
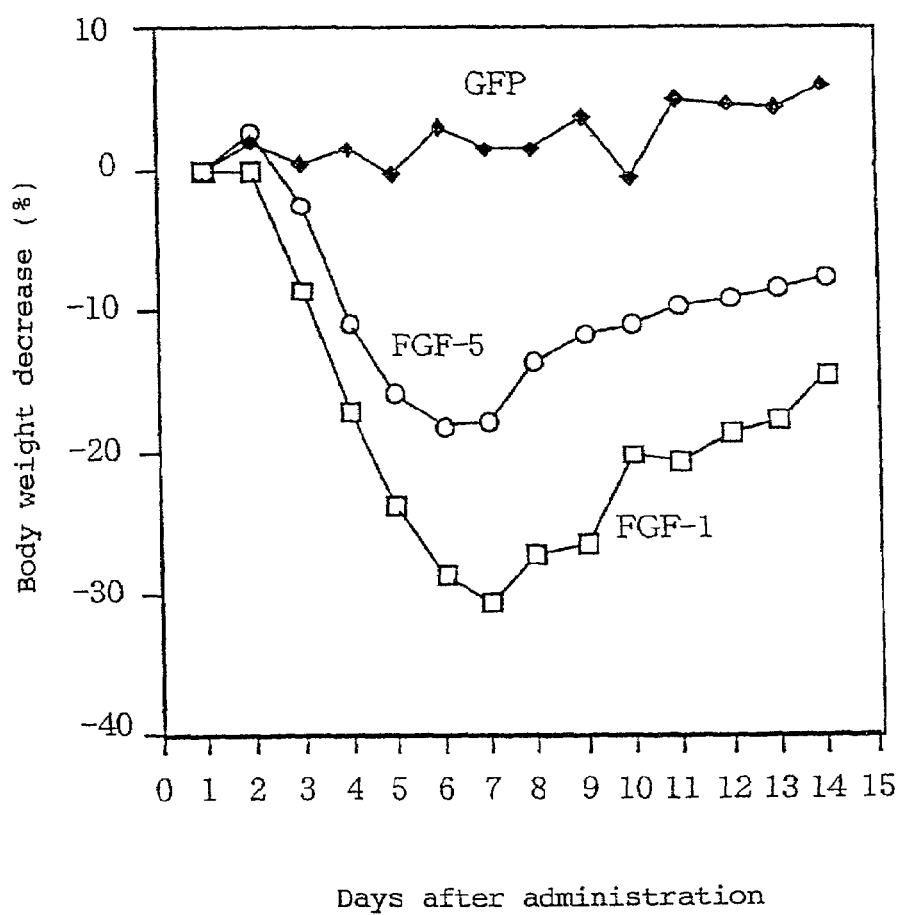
FIG. 6 is a graph showing changes in the body weight of mice after the intraventricular administration of SeV vector expressing FGF-1, FGF-5 and GFP.
Figure 7:
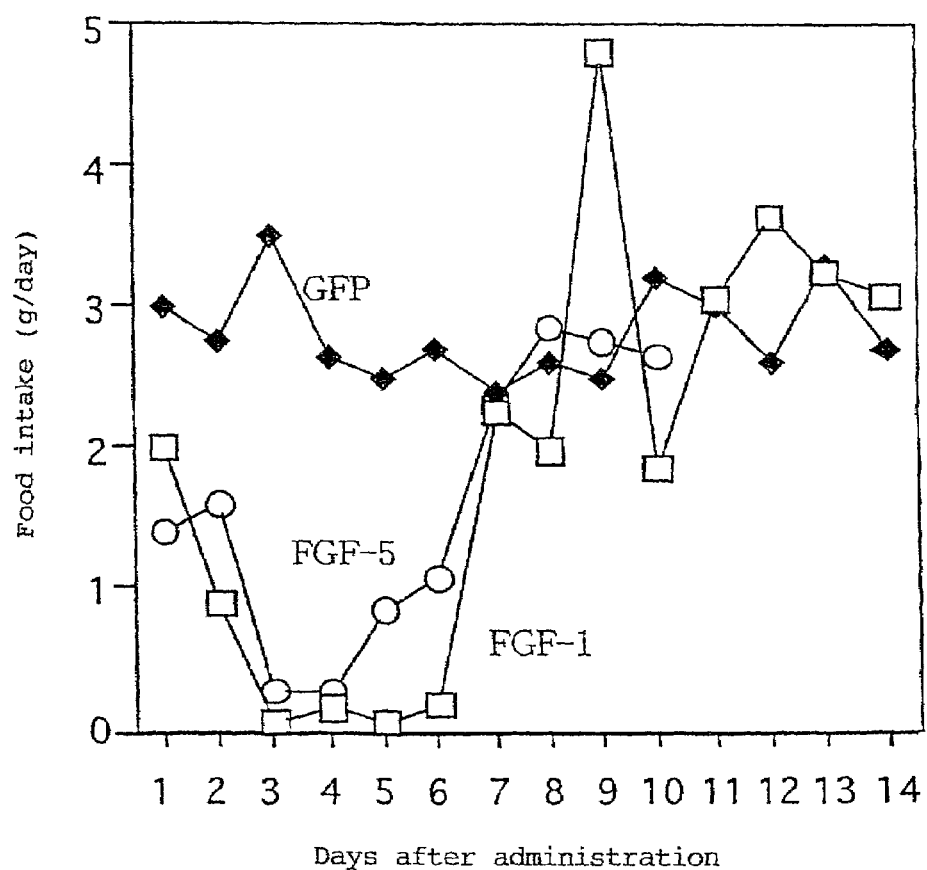
FIG. 7 is a graph showing changes in the amount of food intake of mice after the intraventricular administration of SeV vector expressing FGF-1, FGF-5 and GFP.

The control mice administered with GFP/SeV showed no decrease in the body weight, but showed a 7.5% increase as compared with the weight measured prior to the administration (FIG. 6). The amount of the food intake was also not significantly changed (FIG. 7). In the FGF-1/SeV-administered group, an average 30.5% decrease in the body weight was observed 6 days after the administration (FIG. 6). Then, the body weight turned to increase, resulting in a 13.5% decrease weight 2 weeks later. The change in the amount of food intake due to the FGF-1 administration was so dramatic that almost no food intake was observed from day 2 to day 6, especially from day 3 to day 6 after the administration (FIG. 7) In the FGF-5/SeV vector administered group, although the decrease in the body weight was also observed, the rate of decrease was smaller as compared with the FGF-1/SeV-administrated group, and a 17.9% decrease at the maximum (FIG. 6). The effect on the body weight decrease was in a tendency similar to that obtained in the gerbil experimental system. Although the effect of the FGF-5/SeV vector administration on the body weight decrease was smaller than that of the FGF-1/SeV vector administration, the decrease in the food intake was clearly observed (FIG. 7).

As shown in the results of the example, the effect of the intraventricular expression of FGF induced by SeV vector on the body weight decrease was a 30% decrease at the maximum. Considering that the effect of the intraventricular injection of FGF in the purified protein form on the decrease in the body weigh was 7 to 8% at most, the rate of 30% achieved in the present invention was shown to be extremely high. Difference in these effects may be due to the difference in the intraventricular accumulation of FGF depending on the administration methods, but there is another possibility that this difference is due to a direct action of FGF on nerve cells through the SeV vector infection to ependymal cells. As to the feeding control in the brain, only the control by the hypothalamic nuclei has been reported. In view of this, it is inferred that SeV vector efficiently infects ependymal cells to secrete a functional protein into the cerebrospinal fluid in the ventricle, and that said secretory protein efficiently acts on the hypothalamic nuclei to exert the feeding control. This inference would be supported by the facts that a part of the hypothalamic nerve tissue has a nerve construction with the tight junctions of the blood-brain barrier being lost and contains neurons to receive humoral factors in the peripheral circulation and cerebrospinal fluid.

Among the hypothalamic nuclei, chemosensitive neurons are present in the ventromedial hypothalamus (VMH) and lateral hypothalamic area (LHA), which are thought to be the feeding and satiety centers, and the neuron activity alters in response to metabolic products and hormones contained in blood and cerebrospinal fluid. These VMH and LHA neurons to respond to glucose, and certain cytokines and growth factors are also known to function as appetite regulators. In addition, it has been demonstrated that, from the disruption experiment, the paraventricular nucleus (PVN) is also responsible for suppression of food intake. This nucleus has neurons that produce corticotropin releasing hormone (CRH) and shows the eating depression and activation of sympathetic nerve activity. Furthermore, the arcuate nucleus (ARC) is the site to produce neuropeptide Y (NPY), a food intake stimulator, which is suggested to target PVN. The results of the experiments on the control of eating behavior described herein suggest that FGF acted on these nuclei. Attention should be paid on the relation with leptin, which is expressed in mature adipocytes having lipid droplets and has been extensively studied in relation to eating behaviors as well as NPY, etc.

EXAMPLE 10

Experiment on Suppression of Ischemic Cell Loss by Using Gerbils

The area exposed to brain ischemia undergoes cell damage, and is further led to the cell death as the ischemia progresses. The extent of cell death depends on the degree and duration of ischemia. In the case of severe ischemia, not only nerve cells but also all constitutive cells in the ischemic area sustain irreversible injuries in a short period of time, resulting in the formation of brain infarction focus caused by necrosis. However, in the case of severe ischemic stress of short duration, or in the case of slight ischemia of long duration, the cells in the ischemic region become fragile depending on the severity of ischemia. The most fragile cells are nerve cells, and then oligodendrocytes follow. Astroglia, microglia, and vascular endothelial cell have been known to be more resistant to the ischemic stress. From the examination using a diffuse brain ischemia model, it has been known that there are differences in the resistance to ischemic stress among nerve cells. The known most fragile cells include nerve cells of the hippocampus CA1, those of the hilum of dentate gyrus, and those of the vestibular nuclei in the occipital region of head, which show a delayed cell death. The delayed nerve cell death is a good model of selective nerve cell death with high reproducibility independent of the energy insufficiency, contributing a great deal to the elucidation of molecular mechanisms of ischemic cell death. There have been many reports on the experiments using these model systems to examine, for example, what cascade the nerve cells may go through to their death, which step of the cascade is critical to protect the cell, into what type of cell death the delayed nerve cell death is classified, etc.

As the experimental model animals, rats, gerbils and mice are often used. These animals are used to study and treat the pathologic changes in the portions vulnerable to ischemia, such as hippocampus, corpus striatum, etc., induced by causing transient ischemia in the whole brain of the ischemia models for several to several ten minutes. A rat four vessel occlusion model, a rat hypotensive bilateral common carotid artery occlusion model, a bilateral common carotid artery occlusion model of gerbils, etc. are frequently used as the ischemia model. The present inventors carried out an ischemia experiment using a bilateral common carotid artery occlusion model of gerbil. It has been known that in gerbils cell death occurs mainly in most of the pyramidal cells in the hippocampal CA1 area when animals are subjected to a short time (5 min) ischemia. Therefore, the present inventors performed an experiment aiming at prevention of the cell loss after ischemia by introducing into SeV a gene capable of preventing the cell death and administering the resulting complex to the hippocampus of gerbils.

<Preparation of an ischemic cell death model of gerbil>

Experiments were carried out with a bilateral common carotid artery occlusion (5 min) model of gerbil. By occluding (for 5 min) the bilateral common carotid artery of a gerbil, the pyramidal cells of hippocampus are selectively lost 3-5days after the occlusion. However, since this phenomenon is not commonly observed among gerbils, it is necessary to screen gerbils excellent as a model animal from those obtained from a commercial source. The gerbils selected by the screening (obtained from Dr. Maeda, First Department of Anatomy, Osaka City University Medical School) were used for the experiment.

Figure 8:
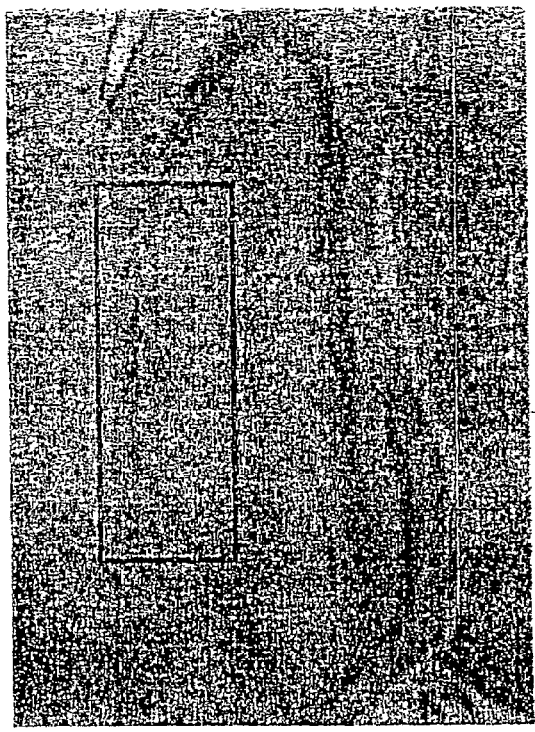
FIG. 8 is micrographs showing the delayed loss of pyramidal cells in the hippocampal CA1 region of a gerbil 5 days after ischemia.
Figure 8:
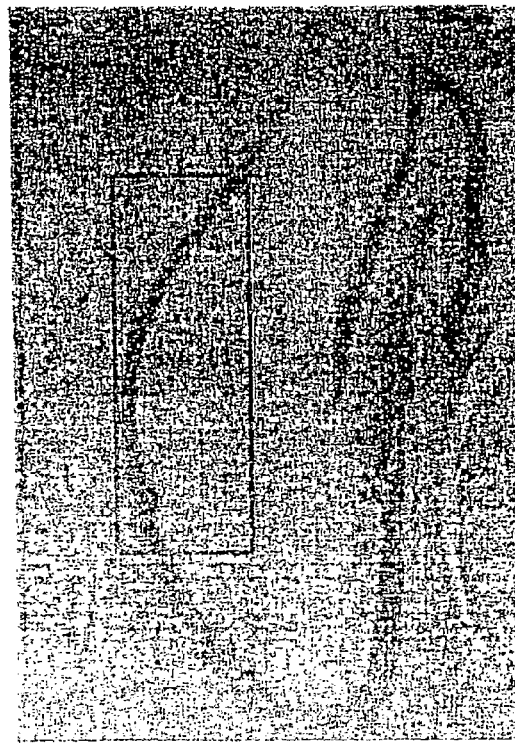

After anesthetizing with ketamine, the animals were subjected to thoracotomy to find out the carotid arteries on the left and right sides of the trachea, and fat adhering to the carotid artery was removed. After the fat removal, the carotid arteries were occluded for 5 min with clips. During this procedure, since the rate of nerve cell death is significantly reduced when the brain and body temperatures are low, the animals were kept warm to retain the body temperature at 38 to 38.5° C. being monitored with a thermometer inserted into the anus. The clips were removed 5 min later, and the blood was perfused again. Five days later, the gerbils were sacrificed, and, after the craniotomy, the brain was excised to prepare tissue slices in paraffin. Conditions of nerve cells were confirmed by toluidine staining. As expected, the loss of the pyramidal cells was observed in the hippocampal CA1 area (FIG. 8). Thus, the ischemic cell death model of gerbil has been prepared.

<Experiment on prevention of nerve cell death by introduction of the recombinant SeV>

The SeV vector prepared above is used to examine whether the SeV vector is effective for preventing the loss of nerve cells as follows: On the day before ischemia, the virus is introduced into only the right brain of the gerbils. Ischemia is applied on the next day, and the animals are sacrificed 5-6 days later to observe the hippocampus pyramidal cells.

<Transfer of FGF-1/SeV into hippocampus>

Gerbils weighing 60 to 80 g were selected and used in this experiment. After anesthetized with Nembutal, the animals were fixed onto a stereotaxic instrument and depilated. The scalp was cut open along the midline of the brain. A hole was made through the skull at the position 5 mm from the bregma and 2 mm to the right of the midline using a dental drill with care not to damage the blood vessels under the cranial bone. After drilling the hole, the dura and such were removed with tweezers. An administration glass needle was inserted into the position at the depth of 1.4 mm, and the animals were allowed to stand for 2 min. Through the glass needle, 0.5 to 1.0 µl of an FGF-1/SeV vector solution (number of viruses $1.0 \times 10^6$ pfu to $2.0 \times 10^6$ pfu) was injected to the position in a period of 12 min, and the animal was allowed to stand for further 10 min. The needle was removed, and the incision was sewed up. In this procedure, the virus was administered only to the right brain, and the loss of nerve cells after ischemia was determined by comparing the right and left brains.

<Induction of Ischemia>

After anesthetizing with ketamine, the animals were subjected to thoracotomy to find out the carotid arteries on the left and right sides of the trachea, and fat adhering to the carotid arteries was removed. After the fat removal, the carotid arteries were occluded for 5 min with clips. During this procedure, since the nerve cell death is significantly reduced when the brain and body temperatures are low, the animals were kept warm to retain at the body temperature at 38 to 38.5° C., being monitored using a thermometer inserted into the anus. The clips were removed 5 min later, and the blood was perfused again. Five to six days later, the animals were sacrificed.

<Preparation of paraffin sections>

After the animal was sacrificed, frontal cross sections of the brain region containing hippocampus were made into 300-500 µm thick slices, soaked in 4% paraformaldehyde overnight, and embedded in paraffin with an automatic apparatus for fixation and embedding. The sections (5 µm thick) were prepared, deparaffinized, and subjected to immnohistochemical staining and other stainings.

<Immunohistochemical staining>

Sections of the FGF-1-administered brain were prepared to examine for the reactivity to an antibody against the virus, to an anti-tubulin antibody (to determine the effect of ischemic operation), to an anti-GFAP antibody (to examine the astrocyte movement), and to an apoptag antibody (to examine the presence of apoptosis). Cells were also subjected to hemotoxylin and eosin (HE) staining to observe the morphological change of cell soma. The results are briefly summarized as follows (Table 2).

TABLE 2

| Determinations of the effect of FGF-1 | Antibody | Determination |
|---|---|---|
| Introduction of the virus into the hippocampal area | anti-SeV antibody | ○ |
| Determination of the effect of the ischemic operation | Anti-β tubulin antibody | ○ |
| Morphology of the soma | HE staining | ○ |
| Movement of astrocytes | Anti-GFAP antibody | ○ |
| Presence of apoptosis | Apoptag | ○ |

Figure 9:
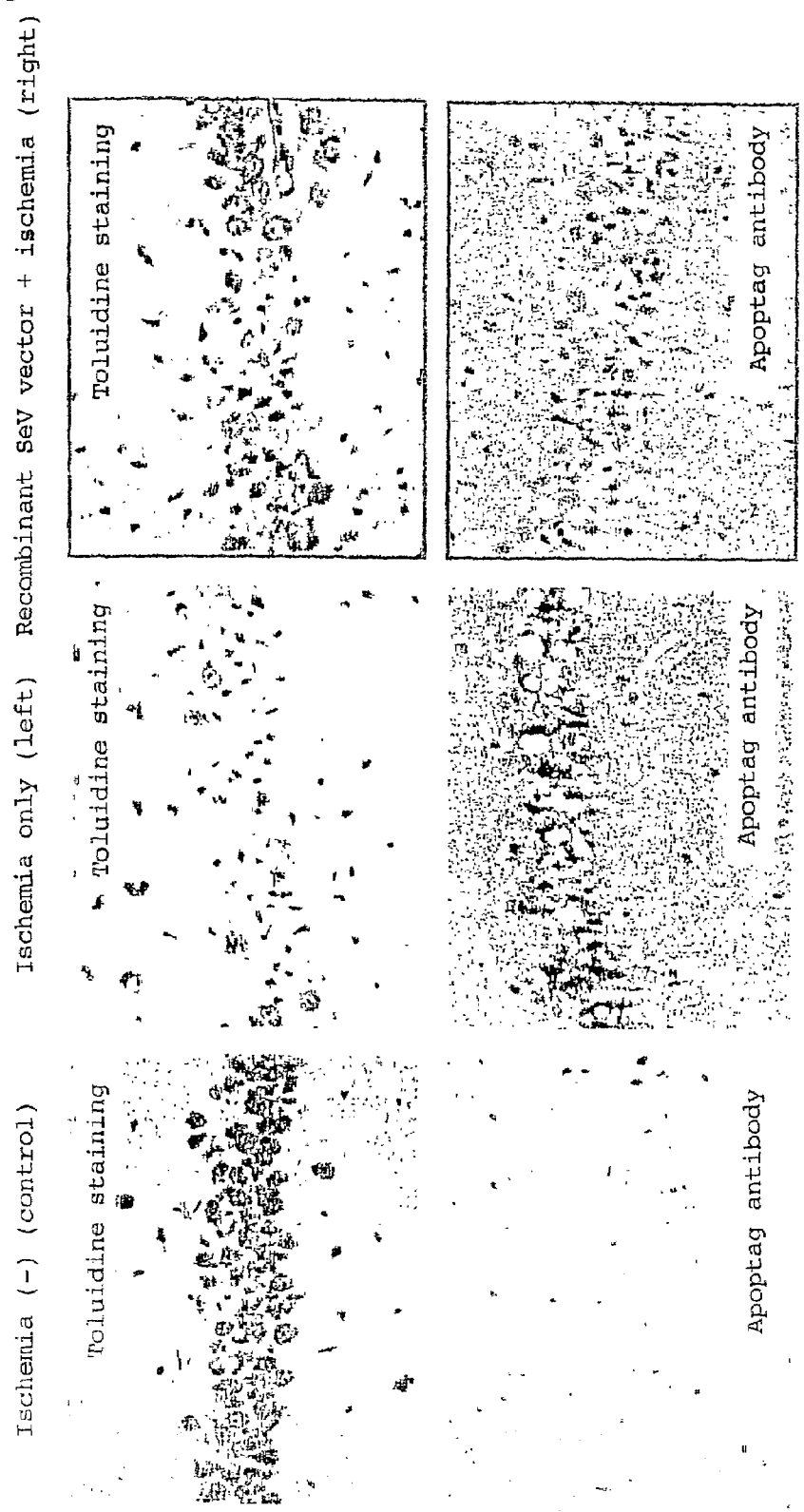
FIG. 9 is micrographs showing the prevention of delayed loss of pyramidal cells in hippocampal CA1 region after the administration of a FGF-1 expressing SeV vector.

In the pyramidal cells of the hippocampal CA1 region, HE staining did not reveal any changes in the nerve cells in the control sample, which underwent no ischemia. Many of the cells in one side of the brain which underwent ischemia but were not administered with the virus were atrophic nerve cells displaying nuclear condensation and eosinophilic change in the cytoplasm, so-called ischemic changes. In contrast, in the other side of the brain, which underwent ischemia and was administered with the virus, a small number of deformed nerve cells were observed to be dispersed, but a majority of the nerve cells retained the original morphology. On the side to which the virus was administered, a region that was positive for the antibody against the virus was observed. In the nerve cells that underwent ischemia but were not administered with the virus, the most of the cells that showed deformation were positive for the apoptag-staining. In contrast, in the cells which underwent ischemia and were administered with the virus, only a very few cells which showed the morphological change in HE staining were positive for the apoptag-staining, indicating that apoptosis was suppressed in the majority of the cells in this side (FIG. 9).

EXAMPLE 11

Protection of Ischemic Nerve Cell Death in Gerbils by GDNF/SeV Administered Via Cerebral Ventricles In this example, protection of ischemic nerve cell death in gerbils by GDNF/SeV administered via cerebral ventricles will be described. A gerbil ischemic nerve cell death model was prepared using the same technique described in Example 10, except for the following two points: (1) the use of the GDNF as the gene carried by the virus, and (2) the use of the cerebral ventricle as the virus administration route.

GDNF (glial cell line-derived neurotrophic factor) was isolated and purified in 1993 as a specific neurotrophic protein for survival of dopaminergic neurons of midbrain nigra. It is a glycoprotein having a molecular weight ranging from 18 to 42 kDa, forming a dimer by an S-S bond. Amino acid sequence homology indicates that it belongs to the transforming growth factor (TGF)-β superfamily. It has a physiological activity of stimulating dopamine uptake by dopaminergic neurons. It has been reported that GDNF also has the neurotrophic activity against the motor, sensory, and autonomic nervous systems. It is also said to have the function of supporting the survival of various peripheral and central neurocytes. As to the prevention of delayed nerve cell death following brain ischemia, effects of GDNF have been already reported in the rat middle cerebral artery (MCA) occulusion model using an adenoviral vector (Kitagawa, H. et al., J. Cereb. Blood Flow Metab. 19(12): 1336-1344, 1999), and in gerbils (Yagi, T. et al., Brain Res. 885(2): 273-282, 2000).

Intraventricular administration was thought to further reduce a possible invasion due to the parenchymal administration of viral vectors using FGF/SeV, and was carried out taking practical intraspinal administration into consideration.

Infection efficiency of SeV to ependymal cells is so high due to the high sialic acid content in their SeV receptor that a high expression level of the protein is obtained with low doses of the SeV vector. As a result, demyelination caused by gliosis as reported for the administration of adenovirus vectors, is expected to decrease.

Example experiments are described below.

<Construction and reconstitution of the recombinant Sendai virus vector containing the human GDNF gene>

The recombinant Sendai virus vector was constructed similarly as in Example 1 according to the method described in literatures (Kato, A. et al., EMBO J. 16: 578-598, 1997; Hasan, M. K. et al., J. Gen. Virol. 78: 2813-2820, 1997).

First, an 18 bp spacer sequence having the NotI restriction site [5'-(G)-CGGCCGCAGATCTTCACG-3'] (SEQ ID NO: 4) was inserted into the contiguous loci between the leader sequence and 5'-terminus of the nucleotide sequence encoding the N protein of the cloned Sendai virus genomic cDNA [pSev(+)] to obtain the plasmid pSeV18+b(+) containing the self-cleaving ribozyme site derived from the antigenomic strand of hepatitis delta virus. To insert the hGDNF gene (containing the stop codon; 636 bp) into the NotI site of the plasmid pSeV18+b(+), primers containing the NotI site and an additional set of Sendai virus E and S signal sequence tags 5'-ACTTGCGGCCGCCAAAGTTCATCTAT-GAAGTTATGGGATGTCGTGGC-3' (SEQ ID NO: 5) and 5'-ACTTGCGGCCGCGATGAACTTTCAC-CCTAAGTTTTTCTTACTACGGT CAGATACATCCA CACCTTTTAGCGG-3' (SEQ ID NO: 6) were prepared (NotI site underlined). Human GDNF gene fragments were amplified by the polymerase chain reaction using these primers and human GDNF gene as the template, and inserted into the NotI site of the plasmid containing SeV genomic cDNA. Plasmid containing the template sendai virus genome containing the GDNF gene and the plasmids (pGEM-N), pGEM-P, and pGEM-L) encoding N-protein, P-protein and L-protein, respectively, were complexed with the commercially available active type dendrimer molecule (SuperFect Transfection Reagent; Qiagen). LLCMK2 cells were transformed together with the above-prepared complexes and the vaccinia virus vT7-3 (Fuerst, T. R. et al., Proc. Natl. Acad. Sci. USA 83: 8122-8126, 1986; Kato, A. et al., Genes Cells 1: 569-579, 1996). After 40 h, cells were disrupted by repeating freezing and thawing three times, and injected into the chorioallantoic membrane of a chicken egg containing a 10-day-old embryo. Then, the virus was recovered, and the vaccinia virus was eliminated by passage in eggs. The virus titer was determined by the hemagglutination activity (HA) (Kato, A. et al., 1996, Genes Cells 1: 569-579) using chicken erythrocytes, and the chorioallantoic fluid containing the virus was stored as the recombinant Sendai virus vector-containing composition of this invention at −80° C.

<The administration of the virus vector>

Gerbils weighing 60 to 80 g were selected and used in this experiment. After anesthetizing with ketamine, the animals were fixed onto a stereotaxic instrument, were depilated, and the scalp was incised along the midline of the brain. A hole was made through the skull at the position 1.0 mm from the bregma and 1.0 mm to the left of the midline using a dental drill. After the duramater and such were removed, a 10-μl Hamilton syringe with a gauge 30 needle was inserted into the depth of 2.0 mm, and a 5-μl virus sample solution (number of viruses 5×10$^6$ pfu) was injected for 5 min. Then, the animal was left aside for a further 5 min. The needle was removed, and the incision was sewed up. As the control, SeV vector encoding the green fluorescent protein (GFP/SeV) was used.

<Induction of Ischemia>

Ischemia was induced 4 days after vector administration. After anesthetizing with ketamine, gerbils were subjected to thoracotomy, and fat adhering to the carotid arteries on the left and right sides of the trachea was removed. After the fat removal, bilateral common carotid arteries were occluded for 5 min with clips. After inducing ischemia, to reduce the protective effect of low temperature on nerve cell death, the animals were kept warm retaining the rectum temperature above 38° C. for 15 min. Six days later, brain samples were collected from treated animals.

<Recovery of brain tissues and preparation of tissue slices>

These procedures were performed according to the methods described in Example 10.

<Results>

This experiment was performed to assess the effect of intraventricular administration of GDNF/SeV on the prevention of delayed nerve cell death of the hippocampal CA1 pyramidal cells caused by ischemia induced 4 days after the aforementioned administration.

Figure 10:
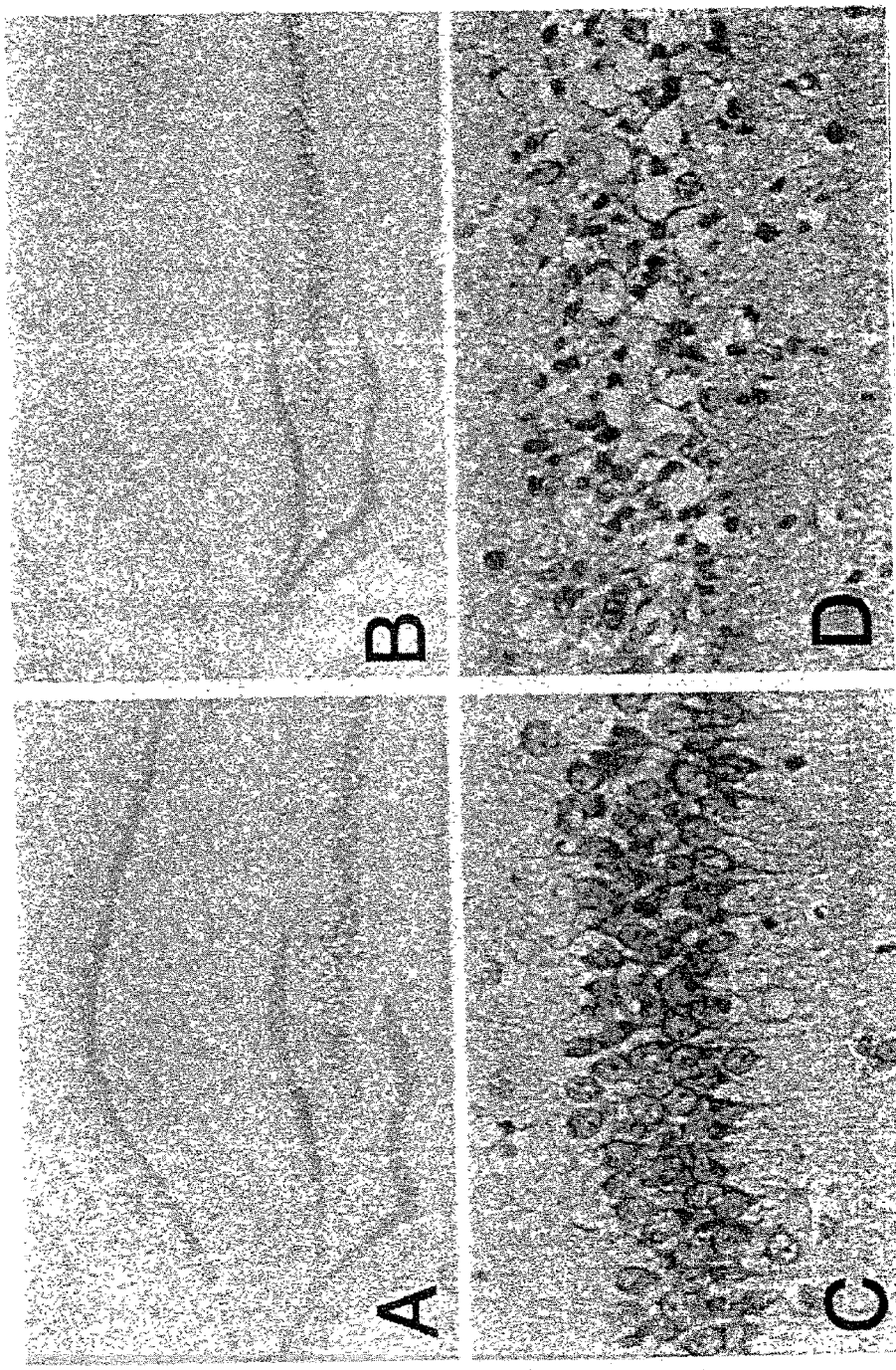
FIG. 10 represents nerve cell-protective effects of GDNF/SeV administration on delayed nerve cell death in the hippocampal CA1 region caused by transient global forebrain ischemia. A), C) GDNF/SeV-administered groups; B), D) GFP/SeV-administered groups. Staining was done using Toluidine blue.
Figure 11:
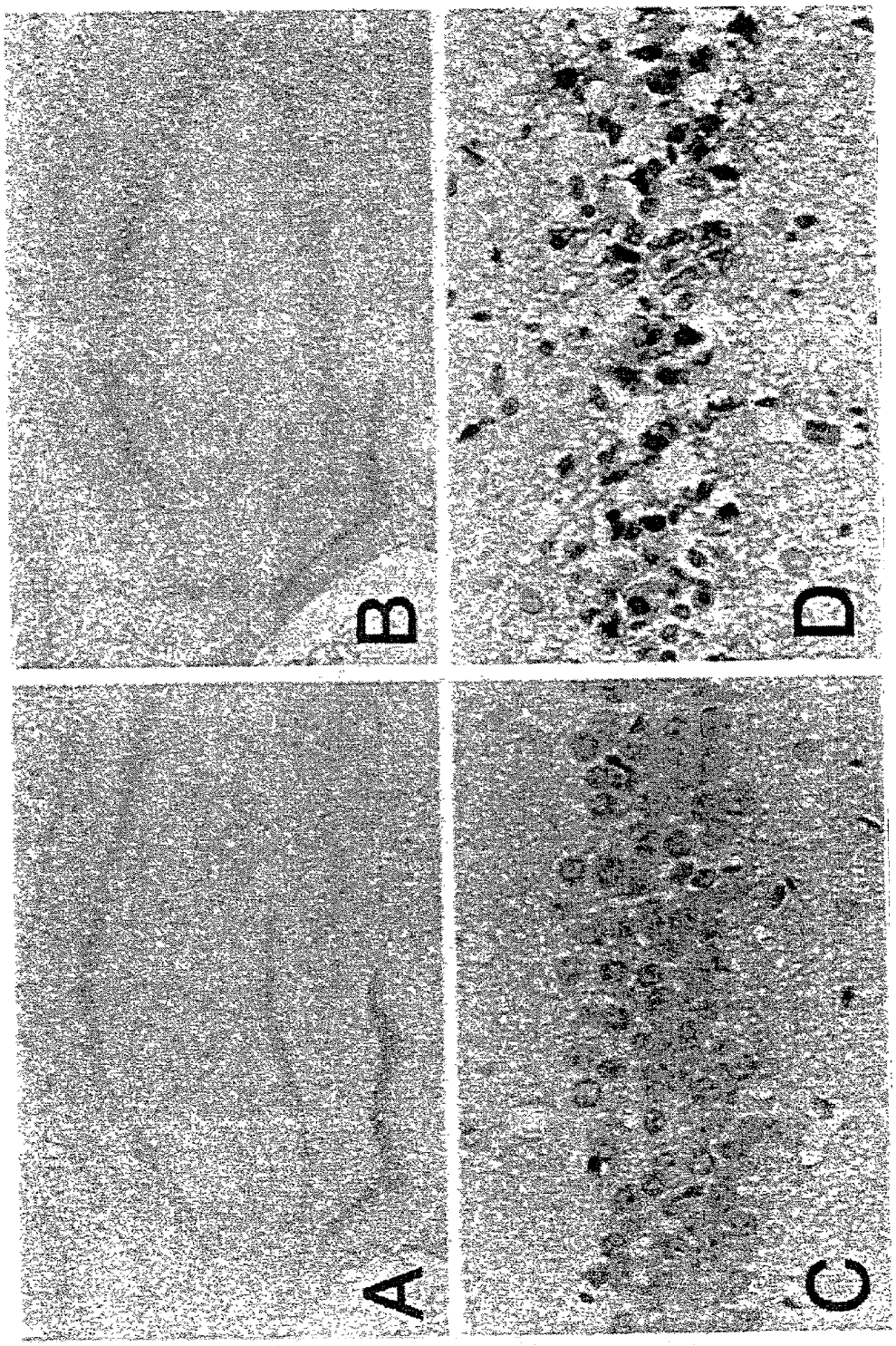
FIG. 11 represents the detection of delayed neural death in the hippocampal CA1 region using the TUNEL (terminal deoxynucleotidyl transferase-mediated dUTP-biotin in situ nick labeling) staining. A), C): GDNF/SeV-administered groups; B), D): GFP/SeV-administered groups. As a counter staining, hematoxylin eosin staining was used.
Figure 12:
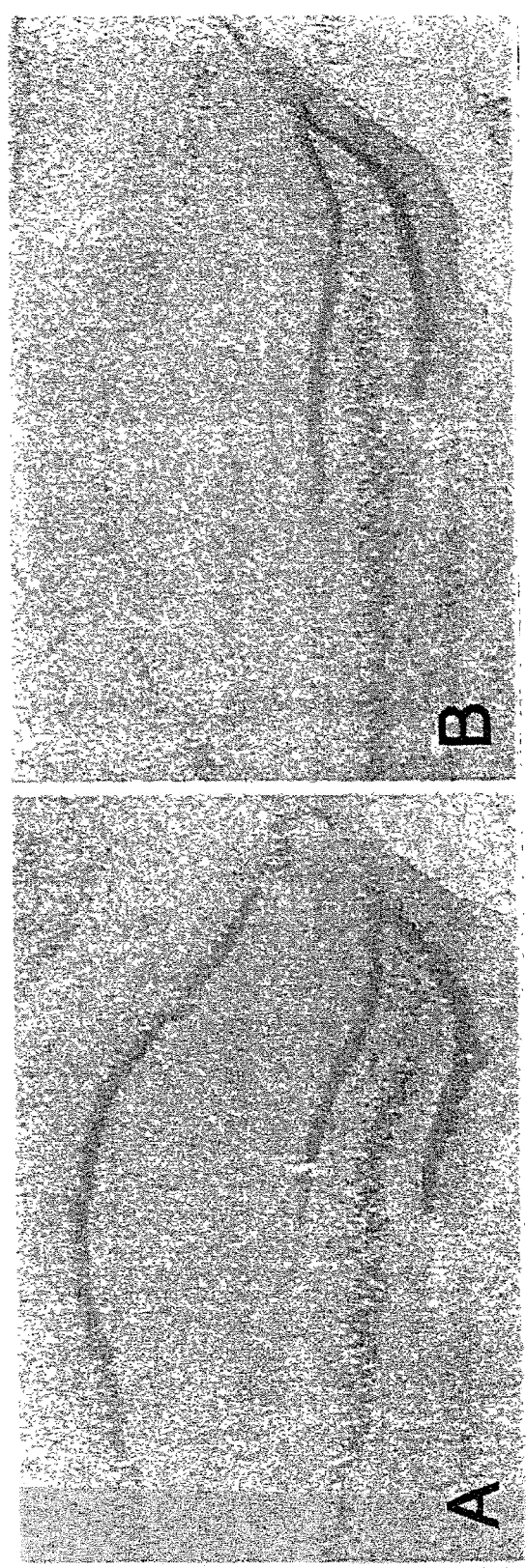
FIG. 12 shows nerve cell-protecting effects of GDNF/SeV administration at the contralateral side of administration. A) GDNF/SeV-administered groups; B) GFP/SeV-administered groups. Staining was done using Toluidine blue.

In a group administered with GFP/SeV used as the control virus vector, nerve cell death accompanying cell atrophy, which was shown by a dense staining of toluidine blue, was observed in almost all pyramidal cells on both sides of the CA1 region (FIGS. 10 and 11). On the other hand, in the group administered with GDNF/SeV, no nerve cell death in pyramidal cells of CA1 region was observed on the contralateral side as well as on the administered side (FIGS. 10 and 12). These results demonstrate that GDNF/SeV administered merely into the lateral ventricle on one side had protecting effects due to the diffusing action of GDNF into the entire ventricle, indicating advantages of intraventricular administration.

Nerve cell death was observed on the inside of the CA1 region, that is, in the subicular CA1 region, indicating that the results of this experiment were not due to errors when inducing ischemia.

A TUNEL-positive reaction was observed only in the CA1 region of animals in the GFP/SeV-administered group, but not in the GDNF/SeV-administered group (FIG. 11), indicating the effective prevention of apoptosis by SeV vector-mediated hGDNF delivery. In addition, almost no increase in astrocytes and microglia cells was detected in the toluidine-stained tissue. These results indicate the validity of this experiment.

Industrial Applicability

The present invention has provided a method for transferring a gene into nerve cells in the tissues including the central nervous tissue, into which transfer of a gene has hitherto been difficult. Use of the method of this invention enables the efficient transfer of a desired gene into the cells in gene therapy, etc.

The invention claimed is:

1. A Sendai viral vector comprising a Sendai viral genome and a foreign gene, wherein the foreign gene is inserted between the R1 and R2 loci of the Sendai virus and the foreign gene encodes a protein selected from the group consisting of fibroblast growth factors, nerve growth factors, apoptosis inhibitors, heat shock proteins, peroxidases, and neurotrophic factors.

2. The Sendai viral vector of claim 1, wherein the gene encodes a protein selected from the group consisting of FGF-1, FGF-5, NGF, CNTF, BDNF, GDNF, p35, CrmA, ILP, bc1-2, and ORF 150.

3. The Sendai viral vector of claim 2, wherein the gene encodes a protein selected from the group consisting of FGF-1, FGF-5, and GDNF.

4. The Sendai viral vector of claim 2, wherein the gene encodes a protein selected from the group consisting of FGF-1 and GDNF.

* * * * *